US010617479B2

(12) United States Patent
Itkowitz et al.

(10) Patent No.: US 10,617,479 B2
(45) Date of Patent: Apr. 14, 2020

(54) SYSTEM AND METHOD FOR INTEGRATED SURGICAL TABLE MOTION

(71) Applicant: INTUITIVE SURGICAL OPERATIONS, INC., Sunnyvale, CA (US)

(72) Inventors: Brandon D. Itkowitz, Sunnyvale, CA (US); Paul G. Griffiths, Santa Clara, CA (US); Nitish Swarup, Sunnyvale, CA (US); Kamyar Ziaei, Belmont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/522,261

(22) PCT Filed: Oct. 27, 2015

(86) PCT No.: PCT/US2015/057673
§ 371 (c)(1),
(2) Date: Apr. 26, 2017

(87) PCT Pub. No.: WO2016/069663
PCT Pub. Date: May 6, 2016

(65) Prior Publication Data
US 2017/0333142 A1    Nov. 23, 2017

Related U.S. Application Data

(60) Provisional application No. 62/134,292, filed on Mar. 17, 2015, provisional application No. 62/069,245, filed on Oct. 27, 2014.

(51) Int. Cl.
*G06F 19/00*       (2018.01)
*A61B 34/30*       (2016.01)
*A61G 13/02*       (2006.01)

(52) U.S. Cl.
CPC .............. *A61B 34/30* (2016.02); *A61G 13/02* (2013.01)

(58) Field of Classification Search
CPC ................................ A61B 34/30; A61G 13/02
(Continued)

(56) References Cited

U.S. PATENT DOCUMENTS

| 4,625,837 A | 12/1986 | Zimmer et al. |
| 4,640,663 A | 2/1987 | Niinomi et al. |

(Continued)

FOREIGN PATENT DOCUMENTS

| CN | 2910169 Y | 6/2007 |
| CN | 101049248 A | 10/2007 |

(Continued)

OTHER PUBLICATIONS

Extended European Search Report for Application No. EP15854253, dated May 11, 2018, 11 pages.

(Continued)

*Primary Examiner* — Ronnie M Mancho
(74) *Attorney, Agent, or Firm* — Artegis Law Group, LLP

(57) ABSTRACT

A computer-assisted medical device includes a first articulated arm, the first articulated arm having an end effector, a first joint set, a second joint set and a control unit. The control unit configures one or more joints in the first joint set to a floating mode, detects movement of the first joint set caused by a movement of the surgical table, drives the second joint set based on the movement of the surgical table, receives an instrument motion command to move the end effector while the surgical table is moving, and moves the end effector based on the instrument motion command. In some embodiments, the instrument motion command is relative to an imaging coordinate frame. In some embodiments, the imaging coordinate frame is based on a pose of (Continued)

an imaging device saved prior to the movement of the surgical table.

22 Claims, 10 Drawing Sheets

(58) Field of Classification Search
USPC .................................................. 700/245, 250
See application file for complete search history.

(56) References Cited

U.S. PATENT DOCUMENTS

| | | | |
|---|---|---|---|
| 4,693,665 A | 9/1987 | Friederichs et al. | |
| 4,894,855 A | 1/1990 | Kresse | |
| 4,928,047 A | 5/1990 | Arai et al. | |
| 4,945,914 A * | 8/1990 | Allen | A61B 6/12 600/426 |
| 5,144,213 A | 9/1992 | Sasaki et al. | |
| 5,222,499 A * | 6/1993 | Allen | A61B 6/12 600/426 |
| 5,397,323 A | 3/1995 | Taylor et al. | |
| 5,784,542 A | 7/1998 | Ohm et al. | |
| 5,790,307 A | 8/1998 | Mick et al. | |
| 5,994,864 A | 11/1999 | Inoue et al. | |
| 6,246,200 B1 | 6/2001 | Blumenkranz et al. | |
| 6,471,165 B2 | 10/2002 | Twisselmann | |
| 6,471,167 B1 | 10/2002 | Myers et al. | |
| 6,560,492 B2 | 5/2003 | Borders | |
| 7,089,612 B2 | 8/2006 | Rocher et al. | |
| 7,155,315 B2 | 12/2006 | Niemeyer et al. | |
| 7,189,246 B2 | 3/2007 | Otsuka et al. | |
| 7,720,322 B2 | 5/2010 | Prisco et al. | |
| 7,741,802 B2 | 6/2010 | Prisco et al. | |
| 7,763,015 B2 | 7/2010 | Cooper et al. | |
| 7,837,674 B2 | 11/2010 | Cooper | |
| 7,852,030 B2 | 12/2010 | Kamiya | |
| 8,004,229 B2 | 8/2011 | Nowlin et al. | |
| 8,069,714 B2 | 12/2011 | Ortmaier et al. | |
| 8,226,072 B2 | 7/2012 | Murayama | |
| 8,271,130 B2 | 9/2012 | Hourtash | |
| 8,400,094 B2 | 3/2013 | Schena | |
| 8,464,720 B1 | 6/2013 | Pigazzi et al. | |
| 8,541,970 B2 | 9/2013 | Nowlin et al. | |
| 8,620,473 B2 | 12/2013 | Diolaiti et al. | |
| 8,624,537 B2 | 1/2014 | Nowlin et al. | |
| 8,641,621 B2 | 2/2014 | Razzaque et al. | |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 8,852,208 B2 | 10/2014 | Gomez et al. | |
| 8,918,211 B2 | 12/2014 | Diolaiti et al. | |
| 9,060,678 B2 | 6/2015 | Larkin et al. | |
| 9,078,686 B2 | 7/2015 | Schena | |
| 9,084,623 B2 | 7/2015 | Gomez et al. | |
| 9,102,058 B2 | 8/2015 | Hofmann et al. | |
| 9,107,683 B2 | 8/2015 | Hourtash et al. | |
| 9,138,129 B2 | 9/2015 | Diolaiti | |
| 9,295,524 B2 | 3/2016 | Schena et al. | |
| 9,296,104 B2 | 3/2016 | Swarup et al. | |
| 9,333,042 B2 | 5/2016 | Diolaiti et al. | |
| 9,334,911 B2 | 5/2016 | Kameta et al. | |
| 9,345,544 B2 | 5/2016 | Hourtash et al. | |
| 9,375,284 B2 | 6/2016 | Hourtash | |
| 9,387,593 B2 | 7/2016 | Bonin et al. | |
| 9,415,510 B2 | 8/2016 | Hourtash et al. | |
| 9,468,501 B2 | 10/2016 | Hourtash et al. | |
| 9,469,034 B2 | 10/2016 | Diolaiti et al. | |
| 9,492,235 B2 | 11/2016 | Hourtash et al. | |
| 9,492,927 B2 | 11/2016 | Diolaiti et al. | |
| 9,918,681 B2 * | 3/2018 | Wallace | A61B 6/12 |
| 10,064,689 B2 | 9/2018 | Swarup et al. | |
| 10,226,306 B2 | 3/2019 | Itkowitz et al. | |
| 10,272,569 B2 | 4/2019 | Swarup et al. | |
| 2002/0082612 A1* | 6/2002 | Moll | A61B 34/30 606/130 |
| 2003/0192758 A1 | 10/2003 | Murata et al. | |
| 2006/0025668 A1 | 2/2006 | Peterson et al. | |
| 2007/0013336 A1* | 1/2007 | Nowlin | B25J 9/1682 318/568.21 |
| 2007/0096670 A1 | 5/2007 | Hashimoto et al. | |
| 2007/0185376 A1 | 8/2007 | Wilson et al. | |
| 2007/0270685 A1 | 11/2007 | Kang et al. | |
| 2008/0004633 A1 | 1/2008 | Arata et al. | |
| 2008/0046122 A1* | 2/2008 | Manzo | A61B 1/00149 700/245 |
| 2008/0064921 A1 | 3/2008 | Larkin | |
| 2008/0125649 A1 | 5/2008 | Meyer et al. | |
| 2008/0312529 A1 | 12/2008 | Amiot et al. | |
| 2009/0088774 A1* | 4/2009 | Swarup | A61B 34/37 606/130 |
| 2009/0326324 A1 | 12/2009 | Munoz et al. | |
| 2010/0042097 A1* | 2/2010 | Newton | A61B 18/1445 606/41 |
| 2010/0138183 A1 | 6/2010 | Jensen et al. | |
| 2010/0168762 A1 | 7/2010 | Osawa et al. | |
| 2010/0204713 A1 | 8/2010 | Ruiz et al. | |
| 2010/0228249 A1* | 9/2010 | Mohr | A61B 34/37 606/41 |
| 2010/0228264 A1* | 9/2010 | Robinson | A61B 18/1206 606/130 |
| 2010/0292843 A1 | 11/2010 | Kariyazaki et al. | |
| 2011/0015521 A1 | 1/2011 | Faul | |
| 2011/0071508 A1 | 3/2011 | Duval et al. | |
| 2012/0029694 A1 | 2/2012 | Mueller et al. | |
| 2012/0101508 A1 | 4/2012 | Wook et al. | |
| 2013/0072822 A1 | 3/2013 | Auchinleck et al. | |
| 2013/0085510 A1 | 4/2013 | Stefanchik et al. | |
| 2013/0096701 A1 | 4/2013 | Suorajaervi et al. | |
| 2013/0110129 A1* | 5/2013 | Reid | A61B 34/30 606/130 |
| 2014/0005654 A1* | 1/2014 | Batross | A61B 17/32009 606/33 |
| 2014/0039517 A1 | 2/2014 | Bowling et al. | |
| 2014/0052153 A1* | 2/2014 | Griffiths | A61B 34/70 606/130 |
| 2014/0052154 A1 | 2/2014 | Griffiths et al. | |
| 2014/0055489 A1 | 2/2014 | Itkowitz et al. | |
| 2014/0222207 A1 | 8/2014 | Bowling et al. | |
| 2014/0276887 A1 | 9/2014 | Stein et al. | |
| 2014/0276952 A1* | 9/2014 | Hourtash | B25J 9/1638 606/130 |
| 2014/0305995 A1 | 10/2014 | Shelton, IV et al. | |
| 2014/0316430 A1 | 10/2014 | Hourtash et al. | |
| 2014/0358161 A1 | 12/2014 | Hourtash et al. | |
| 2015/0032126 A1 | 1/2015 | Nowlin et al. | |
| 2015/0051733 A1 | 2/2015 | Nowlin et al. | |
| 2015/0150639 A1 | 6/2015 | Diolaiti et al. | |
| 2015/0224845 A1 | 8/2015 | Anderson et al. | |
| 2016/0081754 A1 | 3/2016 | Kostrzewski et al. | |
| 2017/0079722 A1 | 3/2017 | O'Grady et al. | |
| 2017/0079730 A1 | 3/2017 | Azizian et al. | |
| 2017/0079731 A1* | 3/2017 | Griffiths | A61B 34/30 |
| 2017/0086932 A1 | 3/2017 | Auld et al. | |
| 2017/0112580 A1* | 4/2017 | Griffiths | A61B 90/50 |
| 2017/0312047 A1 | 11/2017 | Swarup et al. | |
| 2017/0333141 A1 | 11/2017 | Itkowitz et al. | |
| 2017/0333145 A1 | 11/2017 | Griffiths et al. | |
| 2017/0333275 A1 | 11/2017 | Itkowitz et al. | |
| 2017/0334067 A1 | 11/2017 | Swarup et al. | |
| 2018/0289427 A1 | 10/2018 | Griffiths et al. | |
| 2018/0338808 A1 | 11/2018 | Swarup et al. | |
| 2019/0142533 A1 | 5/2019 | Itkowitz et al. | |
| 2019/0176327 A1 | 6/2019 | Swarup et al. | |

FOREIGN PATENT DOCUMENTS

| | | |
|---|---|---|
| CN | 101217913 A | 7/2008 |
| CN | 201082167 Y | 7/2008 |
| CN | 101332137 A | 12/2008 |
| CN | 101466342 A | 6/2009 |
| CN | 101472546 A | 7/2009 |

(56) References Cited

FOREIGN PATENT DOCUMENTS

| | | |
|---|---|---|
| CN | 101959656 A | 1/2011 |
| CN | 102046360 A | 5/2011 |
| CN | 101443163 B | 8/2011 |
| CN | 101234033 B | 6/2012 |
| CN | 103221015 A | 7/2013 |
| CN | 104002296 B | 5/2016 |
| EP | 1915963 A1 | 4/2008 |
| EP | 2047805 A1 | 4/2009 |
| EP | 2332477 A2 | 6/2011 |
| EP | 2332479 A2 | 6/2011 |
| EP | 2332482 A2 | 6/2011 |
| JP | H05138583 A | 6/1993 |
| JP | H06278063 A | 10/1994 |
| JP | H0884735 A | 4/1996 |
| JP | H09254079 A | 9/1997 |
| JP | H09300264 A | 11/1997 |
| JP | 2000107200 A | 4/2000 |
| JP | 2004216022 A | 8/2004 |
| JP | 2004538037 A | 12/2004 |
| JP | 2008259607 A | 10/2008 |
| JP | 2010194101 A | 9/2010 |
| JP | 2011212837 A | 10/2011 |
| JP | 2012005557 A | 1/2012 |
| JP | 2012239709 A | 12/2012 |
| WO | WO-2006039092 A2 | 4/2006 |
| WO | WO-2006069288 A2 | 6/2006 |
| WO | WO-2006124390 A2 | 11/2006 |
| WO | WO-2007136770 A2 | 11/2007 |
| WO | WO-2008002830 A2 | 1/2008 |
| WO | WO-2011109041 A1 | 9/2011 |
| WO | WO-2011143016 A1 | 11/2011 |
| WO | WO-2013048957 A1 | 4/2013 |
| WO | WO-2013181503 A1 | 12/2013 |
| WO | WO-2013181507 A1 | 12/2013 |
| WO | WO-2013181516 A1 | 12/2013 |
| WO | WO-2014028703 A1 | 2/2014 |
| WO | WO-2014146095 A1 | 9/2014 |
| WO | WO-2014146107 A1 | 9/2014 |
| WO | WO-2014146113 A1 | 9/2014 |
| WO | WO-2014146119 A1 | 9/2014 |
| WO | WO-2014146120 A1 | 9/2014 |
| WO | WO-2015142798 A1 | 9/2015 |
| WO | WO-2015142930 A1 | 9/2015 |
| WO | WO-2015142943 A1 | 9/2015 |
| WO | WO-2015142947 A1 | 9/2015 |
| WO | WO-2016069648 A1 | 5/2016 |
| WO | WO-2016069655 A1 | 5/2016 |
| WO | WO-2016069659 A1 | 5/2016 |
| WO | WO-2016069660 A1 | 5/2016 |
| WO | WO-2016069661 A1 | 5/2016 |

OTHER PUBLICATIONS

Partial Supplementary European Search Report for Application No. EP15855456.8, dated May 23, 2018, 11 pages.
Extended European Search Report for Application No. EP15854136.7, dated Jun. 7, 2018, 11 pages.
Extended European Search Report for Application No. EP15854260.5, dated Jun. 7, 2018, 8 pages.
Hesse S., et al., "Lexikon Der Elektrischen Antriebstechnik," Festo Didactic GmbH & Co. KG, Jan. 1, 2004, pp. 1-198, XP055260002 [retrieved on Mar. 21, 2016], Retrieved from the Internet:< url:= "http://www.boss.festo-cpx.com/pdf/539265_webprint.pdf">.
Extended European Search Report for Application No. 15855456.8, dated Sep. 25, 2018, 10 pages.
International Search Report and Written Opinion for Application No. PCT/US2015/057656, dated Feb. 1, 2016, 11 pages.
International Search Report and Written Opinion for Application No. PCT/US2015/057658, dated Feb. 1, 2016, 12 pages.
International Search Report and Written Opinion for Application No. PCT/US2015/057664, dated Feb. 1, 2016, 8 pages.
International Search Report and Written Opinion for Application No. PCT/US2015/057669, dated Feb. 1, 2016, 9 pages.
International Search Report and Written Opinion for Application No. PCT/US2015/057670, dated Feb. 1, 2016, 8 pages.
International Search Report and Written Opinion for Application No. PCT/US2015/057671, dated Feb. 1, 2016, 6 pages.
International Search Report and Written Opinion for Application No. PCT/US2015/057673, dated Feb. 1, 2016, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP15855051.7, dated May 3, 2018, 10 pages.
Extended European Search Report for Application No. EP15855097, dated Apr. 25, 2018, 11 pages.
Extended European Search Report for Application No. EP15855351.1, dated Apr. 30, 2018, 9 pages.
Co-pending U.S. Appl. No. 61/954120, filed Mar. 17, 2014.

* cited by examiner

US 10,617,479 B2

SYSTEM AND METHOD FOR INTEGRATED SURGICAL TABLE MOTION

RELATED APPLICATIONS

This application is a U.S. National Stage patent application of International Patent Application No. PCT/US2015/057673 (filed on Oct. 27, 2015), the benefit of which is claimed, and claims priority to U.S. Provisional Patent Application No. 62/069,245 entitled "System and Method for Integrated Surgical Table," which was filed Oct. 27, 2014, and U.S. Provisional Patent Application No. 62/134,292 entitled "System and Method for Integrating Surgical Table Motion," which was filed Mar. 17, 2015, each of which are hereby incorporated by reference in their entirety.

TECHNICAL FIELD

The present disclosure relates generally to operation of devices with articulated arms and more particularly to repositioning articulated arms when moving a patient and allowing instrument control during disturbances to the articulated arms and a moving endoscopic view reference frame.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. These one or more articulated arms and/or end effectors each include a combination of links and articulated joints that support motion of the articulated arms and/or end effectors. In many cases, the articulated joints are manipulated to obtain a desired position and/or orientation (collectively, a desired pose) of a corresponding instrument located at a distal end of the links and articulated joints of a corresponding articulated arm and/or end effector. Each of the articulated joints proximal to the instrument provides the corresponding articulated arm and/or end effector with at least one degree of freedom that may be used to manipulate the position and/or orientation of the corresponding instrument. In many cases, the corresponding articulated arms and/or end effectors may include at least six degrees of freedom that allow for controlling a x, y, and z position (collectively referred to as translational movement) of the corresponding instrument as well as a roll, pitch, and yaw orientation (collectively referred to as rotational movement) of the corresponding instrument. To provide for greater flexibility in control of the pose of the corresponding instrument, the corresponding articulated arms and/or end effectors are often designed to include redundant degrees of freedom. When redundant degrees of freedom are present it is possible that multiple different combinations of positions and/or orientations of the articulated joints may be used to obtain the same pose of the corresponding instrument.

It is often desirable for the surgeon or operating room staff to move a patient on an operating or surgical table relative to the manipulator arms of a computer-assisted device being used as a surgical manipulator assembly in order to improve or optimize access to, or visualization of, the patient's internal anatomy. For example, a surgeon may wish to perform a gravity-assisted retraction of an organ during a surgical procedure. Because the patient's organs will move as the surgical table is tilted, for safety the surgical instruments are removed from the patient prior to moving the surgical table. Then, in many conventional teleoperated surgical systems, to perform such a retraction, the manipulator arms must be undocked from the cannulas coupling the patient to the manipulator arms so that the body openings where the instruments are inserted into the patient can safely move, the surgical table must then be moved into a new position estimated to be suitable for retraction of the targeted organ, and then the instrument reinserted into the body openings. This method can be time consuming and cumbersome. Furthermore, this process may involve several iterations, because the endoscope is generally also removed from the patient before the table is moved to improve safety, such that visualization of the surgical workspace is lost and the new position is typically an educated guess, which may or may not be accurate or sufficient to properly perform the retraction. To avoid repeated iterations, physicians often "overcorrect" and select positions and orientations that are steeper than necessary to ensure that the desired gravity-assisted retraction occurs. This overcorrection may lead to patient safety problems, because certain orientations, such as a head down orientation of the patient, may be poorly tolerated by a patient, and particularly by larger patients who often have difficulty breathing in such an orientation. In addition, because the instruments are removed from the patient and the manipulator arms are removed from the cannulas, the instruments cannot be used by a physician to assist with the retraction, such as may be done in a traditional laparoscopic procedure.

Accordingly, it would be desirable to allow for repositioning of the patient and or articulated arms while the articulated arms are connected to a patient. It would also be desirable for a user to maintain some control over the articulated arms as the patient or the arms are being repositioned. The systems and methods disclosed herein address these problems along with other problems.

SUMMARY

Consistent with some embodiments, a computer-assisted medical device comprises a first articulated arm, the first articulated arm having an end effector, a first joint set, and a second joint set; and a control unit. In some embodiments, the control unit, when coupled to the articulated arm and a surgical table, is configured configure one or more joints in the first joint set to a floating mode; detect movement of the first joint set caused by a movement of the surgical table; drive the second joint set based on the movement of the surgical table; receive an instrument motion command to move the end effector while the surgical table is moving; and move the end effector based on the instrument motion command. In some examples, the instrument motion command is relative to an imaging coordinate frame. In some examples the control unit transforms the instrument motion command from the imaging coordinate frame to a coordinate frame of the end effector. In some examples the imaging coordinate frame is based on a pose of an imaging device saved prior to the movement of the surgical table. In some examples the imaging coordinate frame is a virtual coordinate frame. In some examples, the control unit maintains the imaging coordinate frame in fixed relationship to a table top of the surgical table. In some examples the control unit sends one or more movement commands to one or more joints of the second joint set based on the instrument motion command. In some examples, the control unit is further configured to drive a third joint set in a second articulated arm based on the movement of the surgical table. In some examples the second joint set is driven based on the movement of the surgical table and the control unit is configured to transform the movement of the surgical table in a surgical table coordinate frame into a motion in an end effector coordinate frame and drive the second joint set to move in relation to the motion in the end effector coordinate frame.

In some embodiments, a method of controlling motion in a medical device comprises configuring one or more joints in a first joint set of a first articulated arm of the medical device to a floating mode, detecting movement of the first joint set caused by movement of a surgical table, receiving data related to the movement of the surgical table, driving a second joint set of the first articulated arm based on the received data, receiving an instrument motion command to move an end effector of the first articulated arm while the surgical table is moving, and moving the end effector based on the instrument motion command.

In some embodiments a non-transitory machine-readable medium comprises a plurality of machine-readable instructions which when executed by one or more processors associated with a medical device are adapted to cause the one or more processors to perform a method comprising configuring one or more joints in a first joint set of a first articulated arm to a floating mode, detecting movement of the first joint set caused by a surgical table, receiving data related to the movement of the surgical table, driving a second joint set based on the data related to the movement of the surgical table, receiving an instrument motion command to move the end effector while the surgical table is moving, and moving the end effector based on the instrument motion command.

In some embodiments, a computer-assisted medical device comprises a first articulated arm, the first articulated arm having an end effector. In some embodiments, a control unit, when coupled to the articulated arm and a surgical table, is configured to maintain the orientation and position of the end effector in relation to a table top of the surgical table when the surgical table is moved.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
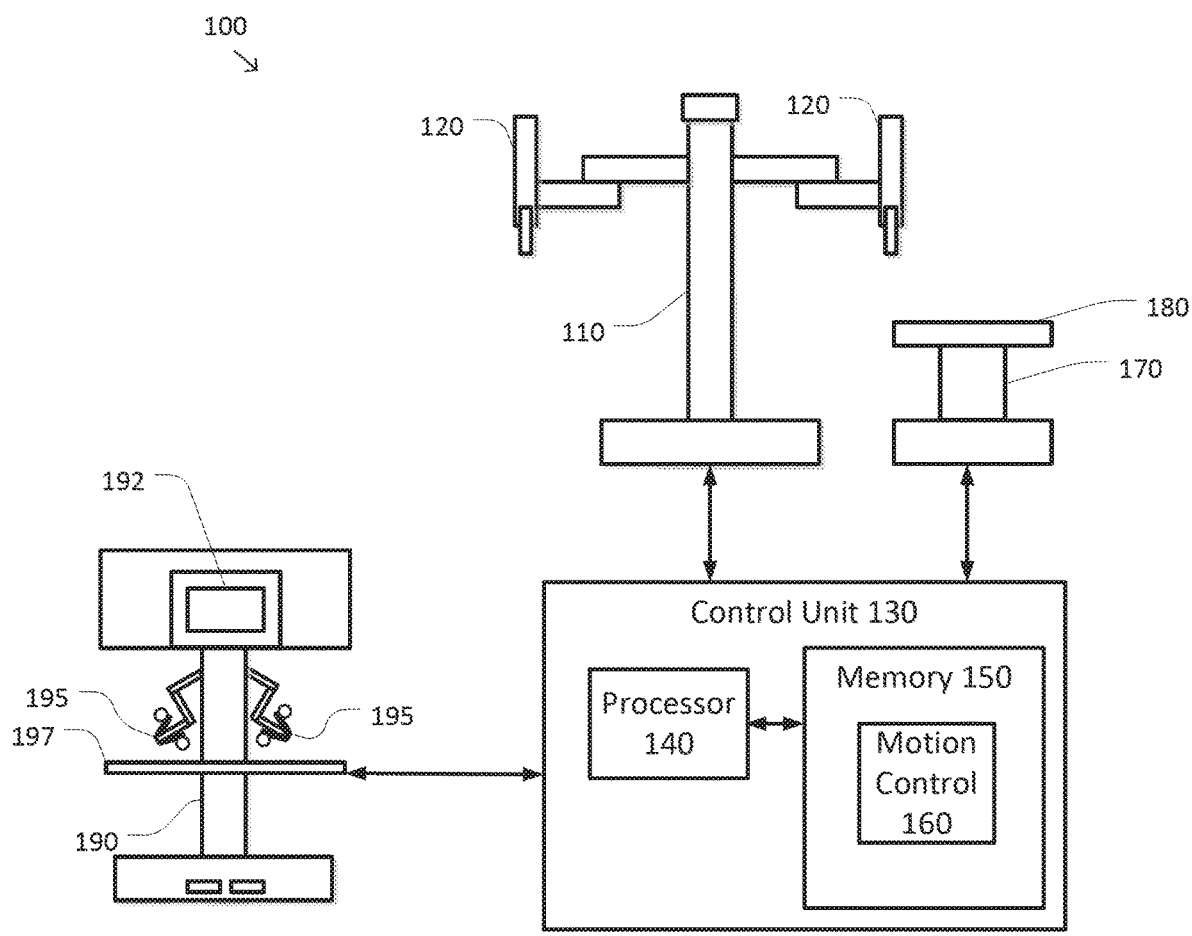
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 supports one or more end effectors. In some examples, device 110 may be consistent with a computer-assisted surgical device. The one or more articulated arms 120 provides support for one or more instruments, surgical instruments, imaging devices, and/or the like mounted to a distal end of at least one of the articulated arms 120. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may optionally be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation. Some examples of control units, such as control unit 130 may include non-transient, tangible, machine readable media that include executable code that when run by one or more processors (e.g., processor 140) may cause the one or more processors to perform the processes of methods 500, 600.

Memory 150 is used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that supports autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 supports articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a surgical table command unit for controlling the position and/or orientation of table top 180. In some embodiments, surgical table 170 may correspond to one or more of the surgical tables commercialized by Trumpf Medical Systems GmbH of Germany.

Surgical table 170 is also coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may plan and/or assist in the planning of motion for surgical table 170 and/or table top 180. In some examples, motion control application 160 may contribute to motion plans associated with collision avoidance, adapting to and/or avoid range of motion limits in joints and links, movement of articulated arms, instruments, end effectors, surgical table components, and/or the like to compensate for other motion in the articulated arms, instruments, end effectors, surgical table components, and/or the like, adjust a viewing device such as an endoscope to maintain and/or place an area of interest and/or one or more instruments or end effectors within a field of view of the viewing device. In some examples, motion control application 160 may prevent motion of surgical table 170 and/or table top 180, such as by preventing movement of surgical table 170 and/or table top 180 through use of the surgical table command unit. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Control unit 130 may further be coupled to an operator workstation 190 via the interface. Operator workstation 190 may be used by an operator, such as a surgeon, to control the movement and/or operation of the articulated arms 120 and the end effectors. To support operation of the articulated arms 120 and the end effectors, operator workstation 190 includes a display system 192 for displaying images of at least portions of one or more of the articulated arms 120 and/or end effectors. For example, display system 192 may be used when it is impractical and/or impossible for the operator to see the articulated arms 120 and/or the end effectors as they are being used. In some embodiments, display system 192 may display a video image from a video capturing device, such as an endoscope, which is controlled by one of the articulated arms 120, or a third articulated arm (not shown).

Operator workstation 190 may further include a console workspace with one or more input controls 195 (or "master controls 195") that may be used for operating the device 110, the articulated arms 120, and/or the end effectors mounted on the articulated arms 120. Each of the input controls 195 may be coupled to the distal end of their own articulated arms so that movements of the input controls 195 may be detected by the operator workstation 190 and communicated to control unit 130. To provide improved ergonomics, the console workspace may also include one or more rests, such as an arm rest 197 on which operators may rest their arms while manipulating the input controls 195. In some examples, the display system 192 and the input controls 195 may be used by the operator to teleoperate the articulated arms 120 and/or the end effectors mounted on the articulated arms 120. In some embodiments, device 110, operator workstation 190, and control unit 130 may correspond to a da Vinci® Surgical System commercialized by Intuitive Surgical, Inc. of Sunnyvale, Calif.

In some embodiments, other configurations and/or architectures may be used with computer-assisted system 100. In some examples, control unit 130 may be included as part of operator workstation 190 and/or device 110. In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms 120 and/or end effectors. Additionally, there may be additional workstations 190 to control additional arms that may be attached to device 110. Additionally, in some embodiments, workstation 190 may have controls for controlling surgical table 170.

Figure 2:
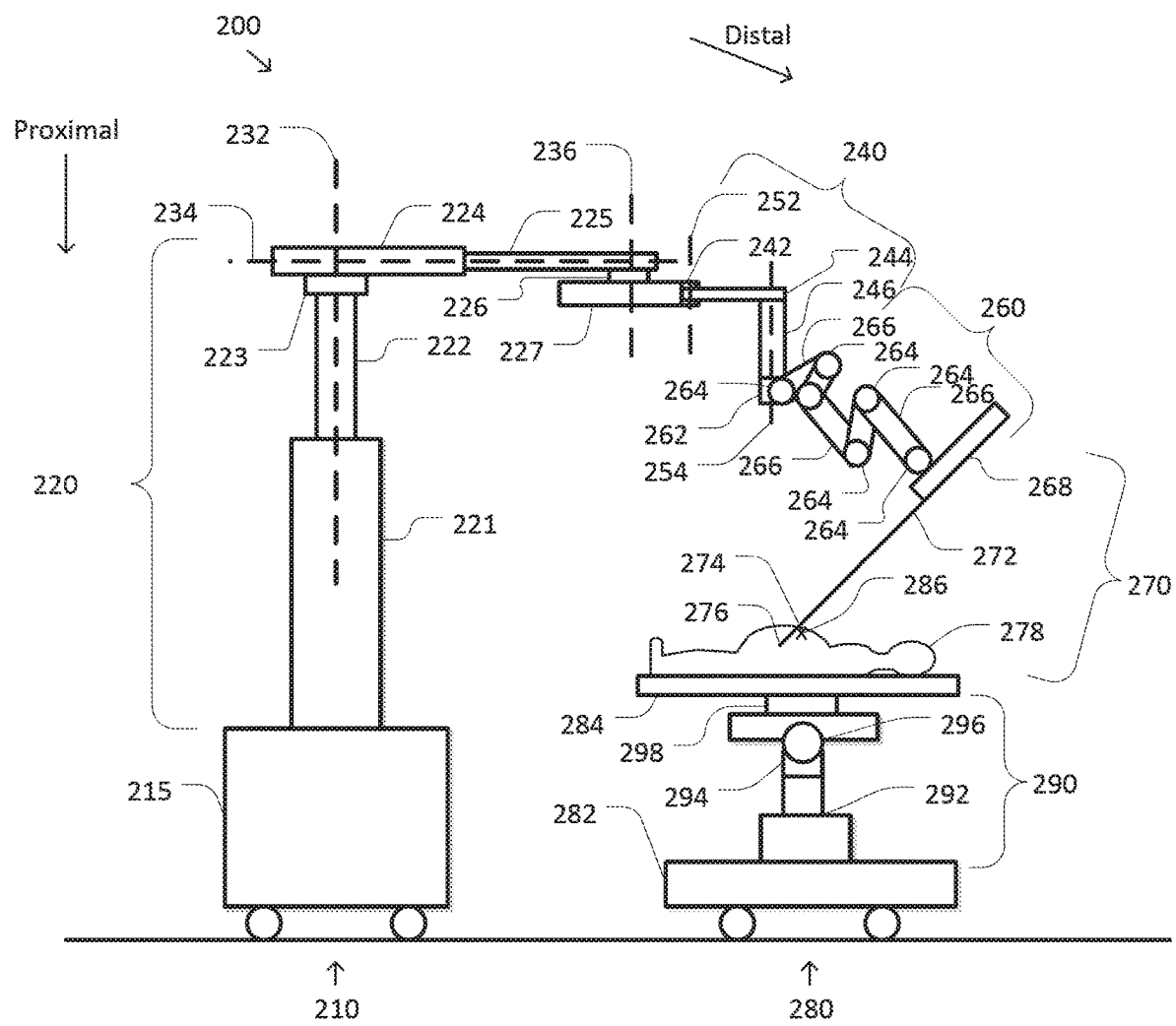
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 may be coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile cart 215 (or "patient-side cart 215") is a set-up structure 220. Coupled to a distal end of the set-up structure is a series of links and set-up joints 240 forming an articulated arm. And coupled to a distal end of the set-up joints 240 is a multi jointed manipulator 260. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 280. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an arm mounting platform 227.

The links and joints of the set-up structure 220 include various degrees of freedom for changing the position and orientation (i.e., the pose) of the arm mounting platform 227. For example, the two-part column is used to adjust a height of the arm mounting platform 227 by moving the shoulder joint 223 up and down along an axis 232. The arm mounting platform 227 is additionally rotated about the mobile cart 215, the two-part column, and the axis 232 using the shoulder joint 223. The horizontal position of the arm mounting platform 227 is also adjusted along an axis 234 using the two-part boom. And the orientation of the arm mounting platform 227 may also adjusted by rotation about an arm mounting platform orientation axis 236 using the wrist joint 226. Thus, subject to the motion limits of the links and joints in the set-up structure 220, the position of the arm mounting platform 227 may be adjusted vertically above the mobile cart 215 using the two-part column. The positions of the arm mounting platform 227 may also be adjusted radially and angularly about the mobile cart 215 using the two-part boom and the shoulder joint 223, respectively. And the angular orientation of the arm mounting platform 227 may also be changed using the wrist joint 226.

The arm mounting platform 227 is used as a mounting point for one or more articulated arms. The ability to adjust the height, horizontal position, and orientation of the arm mounting platform 227 about the mobile cart 215 provides a flexible set-up structure for positioning and orienting the one or more articulated arms about a work space located near the mobile cart 215 where an operation or procedure is to take place. For example, arm mounting platform 227 may be positioned above a patient so that the various articulated arms and their corresponding manipulators and instruments have sufficient range of motion to perform a surgical procedure on the patient. FIG. 2 shows a single articulated arm coupled to the arm mounting platform using a first set-up joint 242 (or "flex joint 242.") And although only one articulated arm is shown, one of ordinary skill would understand that multiple articulated arms may be coupled to the arm mounting platform 227 using additional first set-up joints.

The first set-up joint 242 forms the most proximal portion of the set-up joints 240 section of the articulated arm that is the most proximal to the patient-side cart 215. The set-up joints 240 may further include a series of joints and links. As shown in FIG. 2, the set-up joints 240 may include at least links 244 and 246 coupled via one or more joints (not expressly shown). The joints and links of the set-up joints 240 include the ability to rotate the set-up joints 240 relative to the arm mounting platform 227 about an axis 252 using the first set-up joint 242, adjust a radial or horizontal distance between the first set-up joint 242 and the link 246, adjust a height of a manipulator mount 262 at the distal end of link 246 relative to the arm mounting platform 227 along an axis 254, and rotate the manipulator mount 262 about axis 254. In some examples, the set-up joints 240 may further include additional joints, links, and axes permitting additional degrees of freedom for altering a pose of the manipulator mount 262 relative to the arm mounting platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument or manipulator instrument 270 is mounted to the instrument carriage 268. Instrument 270 includes a shaft 272, which is aligned along an insertion axis. The shaft 272 is typically aligned so that it passes through a remote center of motion 274 associated with the manipulator 260. Location of the remote center of motion 274 is typically maintained in a fixed translational relationship relative to the manipulator mount 262 so that operation of the joints 264 in the manipulator 260 result in rotations of the shaft 272 about the remote center of motion 274. Depending upon the embodiment, the fixed translational relationship of the remote center of motion 274 relative to the manipulator mount 262 is maintained using physical constraints in the joints 264 and links 266 of the manipulator 260, using software constraints placed on the motions permitted for the joints 264, and/or a combination of both. Representative embodiments of computer-assisted surgical devices using remote centers of motion maintained using physical constraints in joints and links are described in U.S. patent application Ser. No. 13/906,888 entitled "Redundant Axis and Degree of Freedom for Hardware-Constrained Remote Center Robotic Manipulator," which was filed May 13, 2013, and representative embodiments of computer-assisted surgical devices using remote centers of motion maintained by software constraints are described in U.S. Pat. No. 8,004,229 entitled "Software Center and Highly Configurable Robotic Systems for Surgery and Other Uses," which was filed May 19, 2005, the specifications of which are hereby incorporated by reference in their entirety. In some examples, the remote center of motion 274 may correspond to a location of a surgical port, body opening, or incision site in a patient 278 when shaft 272 is inserted into the patient 278. Because the remote center of motion 274 corresponds to the body opening, as the instrument 270 is used, the remote center of motion 274 remains stationary relative to the patient 278 to limit stresses on the anatomy of the patient 278 at the remote center of motion 274. In some examples, the shaft 272 may be optionally passed through a cannula (not shown) located at the body opening. In some examples, instruments having a relatively larger shaft or guide tube outer diameter (e.g., 4-5 mm or more) may be passed through the body opening using a cannula and the cannula may optionally be omitted for instruments having a relatively smaller shaft or guide tube outer diameter (e.g., 2-3 mm or less).

At the distal end of the shaft 272 is an end effector 276. The degrees of freedom in the manipulator 260 due to the joints 264 and the links 266 may permit at least control of the roll, pitch, and yaw of the shaft 272 and/or end effector 276 relative to the manipulator mount 262. In some examples, the degrees of freedom in the manipulator 260 may further include the ability to advance and/or withdraw the shaft 272 using the instrument carriage 268 so that the end effector 276 may be advanced and/or withdrawn along the insertion axis and relative to the remote center of motion 274. In some examples, the manipulator 260 may be consistent with a manipulator for use with the da Vinci® Surgical System commercialized by Intuitive Surgical, Inc. of Sunnyvale, Calif. In some examples, the instrument 270 may be an imaging device such as an endoscope, a gripper, a surgical instrument such as a cautery or a scalpel, and/or the like. In some examples, the end effector 276 may include additional degrees of freedom, such as roll, pitch, yaw, grip, and/or the like that allow for additional localized manipulation of portions of the end effector 276 relative to the distal end of shaft 272.

During a surgery or other medical procedure, the patient 278 is typically located on the surgical table 280. The surgical table 280 includes a table base 282 and a table top 284 with the table base 282 being located in proximity to mobile cart 215 so that the instrument 270 and/or end effector 276 may be manipulated by the computer-assisted device 210 while the shaft 272 of instrument 270 is inserted into the patient 278 at the body opening. The surgical table 280 further includes an articulated structure 290 that includes one or more joints or links between the table base 282 and the table top 284 so that the relative location of the table top 284, and thus the patient 278, relative to the table base 282 is controlled. In some examples, the articulated structure 290 may be configured so that the table top 284 is controlled relative to a virtually-defined table motion isocenter 286 that may be located at a point above the table top 284. In some examples, isocenter 286 may be located within the interior of the patient 278. In some examples, isocenter 286 may be collocated with the body wall of the patient at or near one of the body openings, such as a body opening corresponding to remote center of motion 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the isocenter 286. The tilt 294 allows the table top 284 to be tilted side-to-side so that either the right or left side of the patient 278 may be rotated upward relative to the other side of the patient 278 (i.e., about a longitudinal, cranial-caudal, or head-to-toe (cranial-caudal) axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about isocenter 286. The articulated structure 290 further includes additional links and joints 298 to slide the table top 284 along the longitudinal (cranial-caudal) axis back and forth relative to the table base 282 with generally a left and/or right motion as depicted in FIG. 2.

FIGS. 7A-7G are simplified schematic views that illustrate various computer-assisted device system architectures that incorporate the integrated computer-assisted device and movable surgical table features described herein. The various illustrated system components are in accordance with the principles described herein. In these illustrations, the components are simplified for clarity, and various details such as individual links, joints, manipulators, instruments, end effectors, etc. are not shown, but they should be understood to be incorporated in the various illustrated components.

In these architectures, cannulas associated with one or more surgical instruments or clusters of instruments are not shown, and it should be understood that cannulas and other instrument guide devices optionally may be used for instruments or instrument clusters having a relatively larger shaft or guide tube outer diameter (e.g., 4-5 mm or more) and optionally may be omitted for instruments having a relatively smaller shaft or guide tube outer diameter (e.g., 2-3 mm or less).

Also in these architectures, teleoperated manipulators should be understood to include manipulators that during surgery define a remote center of motion by using hardware constraints (e.g., fixed intersecting instrument pitch, yaw, and roll axes) or software constraints (e.g., software-constrained intersecting instrument pitch, yaw, and roll axes). A hybrid of such instrument axes of rotation may be defined (e.g., hardware-constrained roll axis and software-constrained pitch and yaw axes) are also possible. Further, some manipulators may not define and constrain any surgical instrument axes of rotation during a procedure, and some manipulators may define and constrain only one or two instrument axes of rotation during a procedure.

Figure 7A:
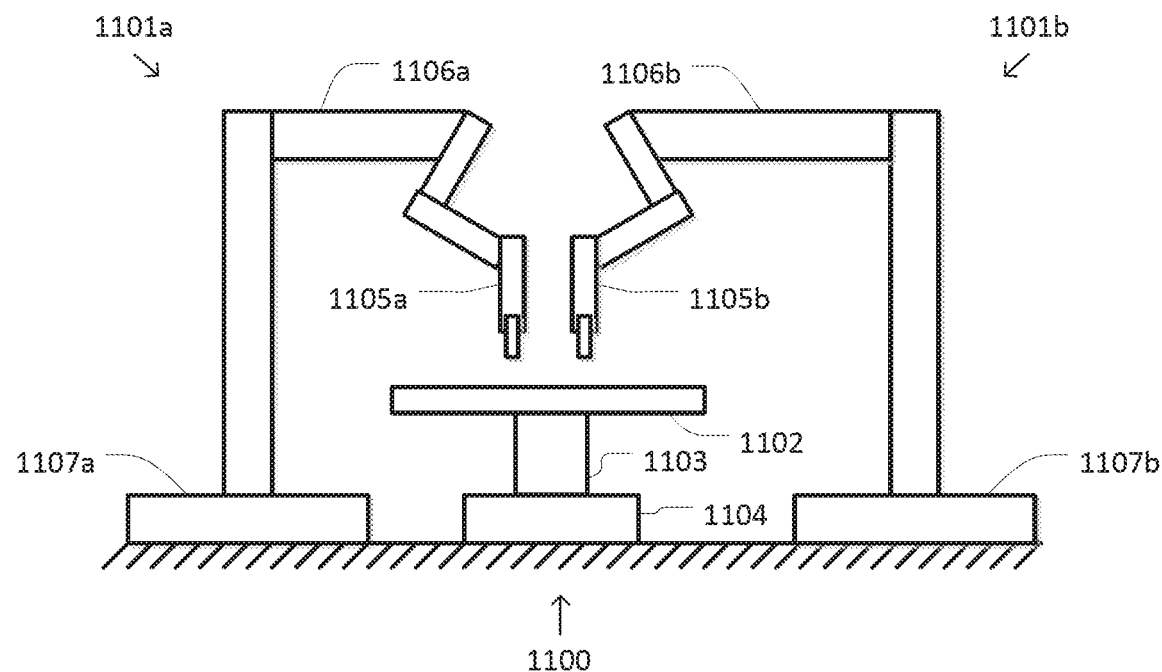
FIGS. 7A-7G are simplified schematic views that illustrate various computer-assisted device system architectures that incorporate the integrated computer-assisted device and movable surgical table features described herein.

FIG. 7A illustrates a movable surgical table 1100 and a single-instrument computer-assisted device 1101a are shown. Surgical table 1100 includes a movable table top 1102 and a table support structure 1103 that extends from a mechanically grounded table base 1104 to support the table top 1102 at a distal end. In some examples, surgical table 1100 may be consistent with surgical table 170 and/or 280. Computer-assisted device 1101a includes a teleoperated manipulator and a single instrument assembly 1105a. Computer-assisted device 1101a also includes a support structure 1106a that is mechanically grounded at a proximal base 1107a and that extends to support manipulator and instrument assembly 1105a at a distal end. Support structure 1106a is configured to allow assembly 1105a to be moved and held in various fixed poses with reference to surgical table 1100. Base 1107a is optionally permanently fixed or movable with reference to surgical table 1100. Surgical table 1100 and computer-assisted device 1101a operate together as described herein.

FIG. 7A further shows an optional second computer-assisted device 1101b, which illustrates that two, three, four, five, or more individual computer-assisted devices may be included, each having a corresponding individual teleoperated manipulator and single-instrument assembly(ies) 1105b supported by a corresponding support structure 1106b. Computer-assisted device 1101b is mechanically grounded, and assemblies 1105b are posed, similarly to computer-assisted device 1101a. Surgical table 1100 and computer-assisted devices 1101a and 1101b together make a multi-instrument surgical system, and they operate together as described herein. In some examples, computer-assisted devices 1101a and/or 1101b may be consistent with computer-assisted devices 110 and/or 210.

Figure 7B:
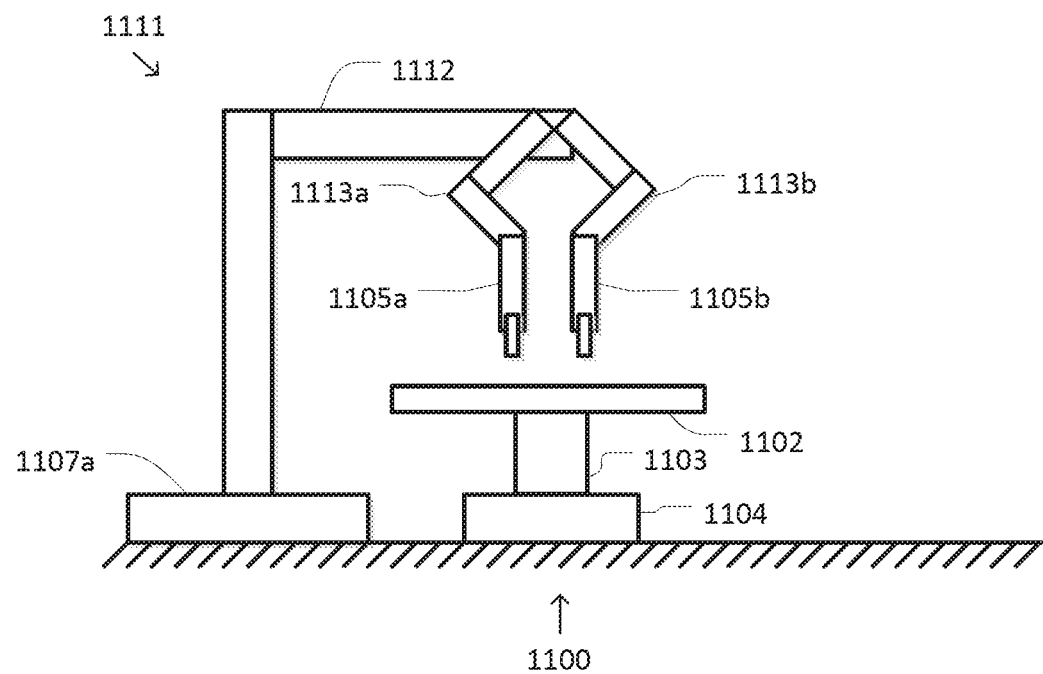

As shown in FIG. 7B, another movable surgical table 1100 and a computer-assisted device 1111 are shown. Computer-assisted device 1111 is a multi-instrument device that includes two, three, four, five, or more individual teleoperated manipulator and single-instrument assemblies as shown by representative manipulator and instrument assemblies 1105a and 1105b. The assemblies 1105a and 1105b of computer-assisted device 1111 are supported by a combined support structure 1112, which allows assemblies 1105a and 1105b to be moved and posed together as a group with reference to surgical table 1100. The assemblies 1105a and 1105b of computer-assisted device 1111 are also each supported by a corresponding individual support structure 1113a and 1113b, respectively, which allows each assembly 1105a and 1105b to be individually moved and posed with reference to surgical table 1100 and to the one or more other assemblies 1105a and 1105b. Examples of such a multi-instrument surgical system architecture are the da Vinci Si® Surgical System and the da Vinci® Xi™ Surgical System, commercialized by Intuitive Surgical, Inc. Surgical table 1100 and a surgical manipulator system comprising an example computer-assisted device 1111 operate together as described herein. In some examples, computer-assisted device 1111 is consistent with computer-assisted devices 110 and/or 210.

Figure 7C:
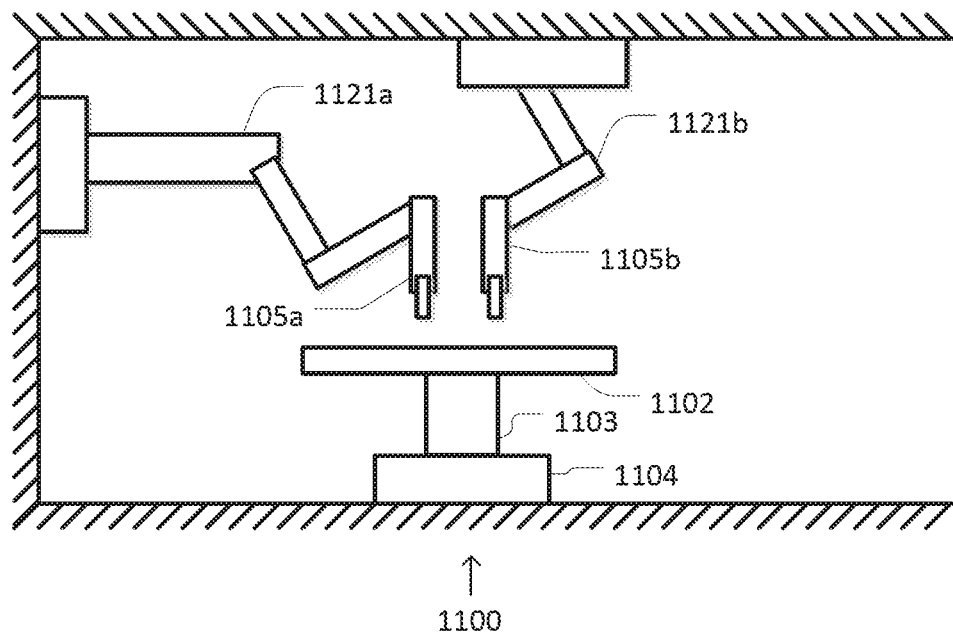

The computer-assisted devices of FIGS. 7A and 7B are each shown mechanically grounded at the floor. But, one or more such computer-assisted devices may optionally be mechanically grounded at a wall or ceiling and be permanently fixed or movable with reference to such a wall or ceiling ground. In some examples, computer-assisted devices may be mounted to the wall or ceiling using a track or grid system that allows the support base of the computer-assisted systems to be moved relative to the surgical table. In some examples, one or more fixed or releasable mounting clamps may be used to mount the respective support bases to the track or grid system. As shown in FIG. 7C, a computer-assisted device 1121a is mechanically grounded at a wall, and a computer-assisted device 1121b is mechanically grounded at a ceiling.

In addition, computer-assisted devices may be indirectly mechanically grounded via the movable surgical table 1100.

Figure 7D:
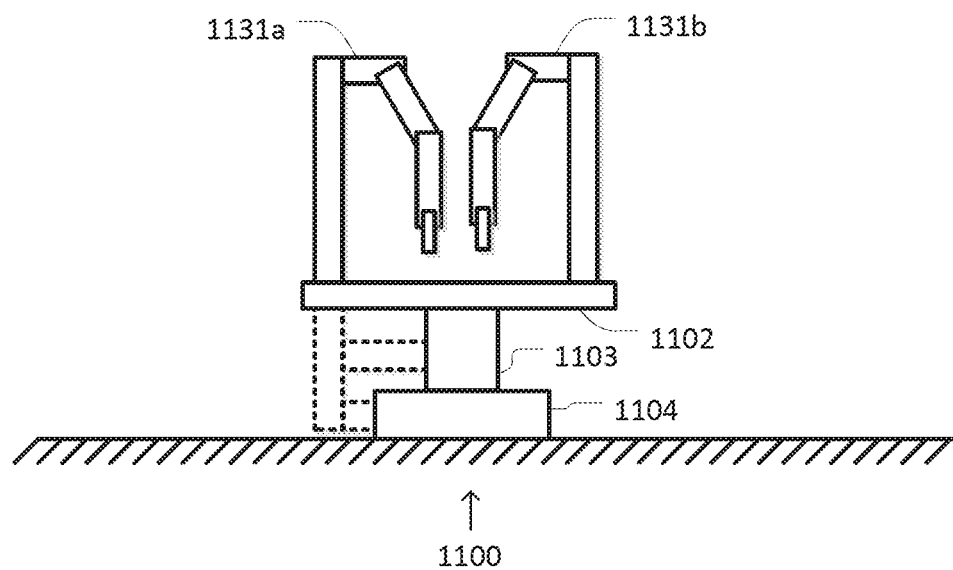

As shown in FIG. 7D, a computer-assisted device 1131a is coupled to the table top 1102 of surgical table 1100. Computer-assisted device 1131a may optionally be coupled to other portions of surgical table 1100, such as table support structure 1103 or table base 1104, as indicated by the dashed structures shown in FIG. 7D. When table top 1102 moves with reference to table support structure 1103 or table base 1104, the computer-assisted device 1131a likewise moves with reference to table support structure 1103 or table base 1104. When computer-assisted device 1131a is coupled to table support structure 1103 or table base 1104, however, the base of computer-assisted device 1131a remains fixed with reference to ground as table top 1102 moves. As table motion occurs, the body opening where instruments are inserted into the patient may move as well because the patient's body may move and change the body opening locations relative to the table top 1102. Therefore, for embodiments in which computer-assisted device 1131a is coupled to the table top 1102, the table top 1102 functions as a local mechanical ground, and the body openings move with reference to the table top 1102, and so with reference to the computer-assisted device 1131a as well. FIG. 7D also shows that a second computer-assisted device 1131b optionally may be added, configured similarly to computer-assisted device 1131a to create a multi-instrument system. Systems that include one or more computer-assisted device coupled to the surgical table operate as disclosed herein.

In some embodiments, other combinations of computer-assisted devices with the same or hybrid mechanical groundings are possible. For example, a system may include one computer-assisted device mechanically grounded at the floor, and a second computer-assisted device mechanically grounded to the floor via the surgical table. Such hybrid mechanical ground systems operate as disclosed herein.

Figure 7E:
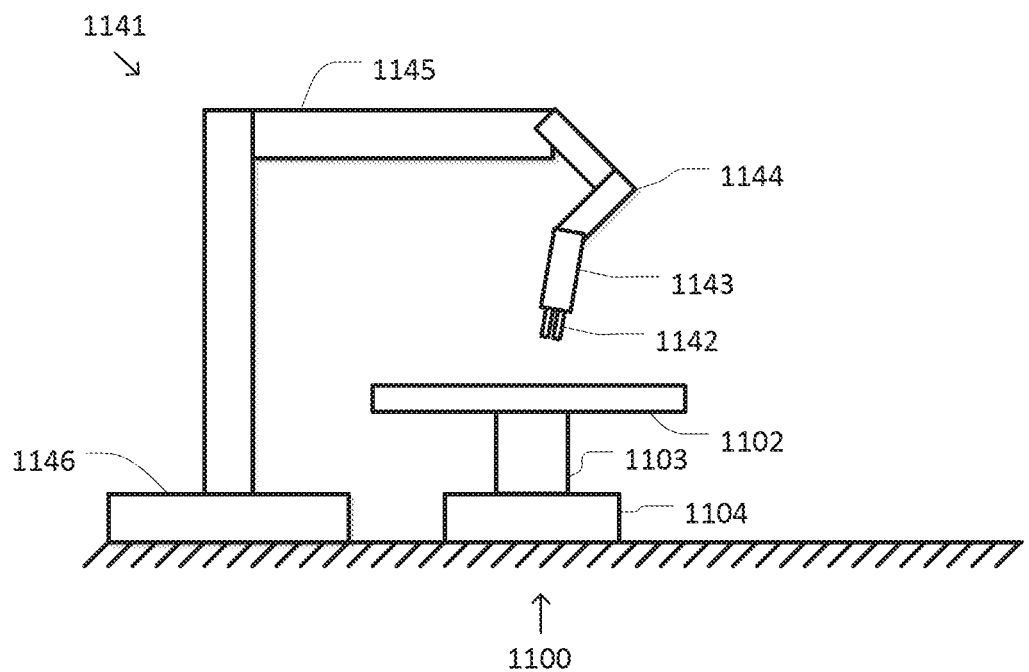

Inventive aspects also include single-body opening systems in which two or more surgical instruments enter the body via a single body opening. Examples of such systems are shown in U.S. Pat. No. 8,852,208 entitled "Surgical System Instrument Mounting," which was filed Aug. 12, 2010, and U.S. Pat. No. 9,060,678 entitled "Minimally Invasive Surgical System," which was filed Jun. 13, 2007, both of which are incorporated by reference. FIG. 7E illustrates a teleoperated multi-instrument computer-assisted device 1141 together with surgical table 1100 as described above. Two or more instruments 1142 are each coupled to a corresponding manipulator 1143, and the cluster of instruments 1142 and instrument manipulators 1143 are moved together by a system manipulator 1144. The system manipulator 1144 is supported by a support assembly 1145 that allows system manipulator 1144 to be moved to and fixed at various poses. Support assembly 1145 is mechanically grounded at a base 1146 consistent with the descriptions above. The two or more instruments 1142 are inserted into the patient at the single body opening. Optionally, the instruments 1142 extend together through a single guide tube, and the guide tube optionally extends through a cannula, as described in the references cited above. Computer-assisted device 1141 and surgical table 1100 operate together as described herein.

Figure 7F:
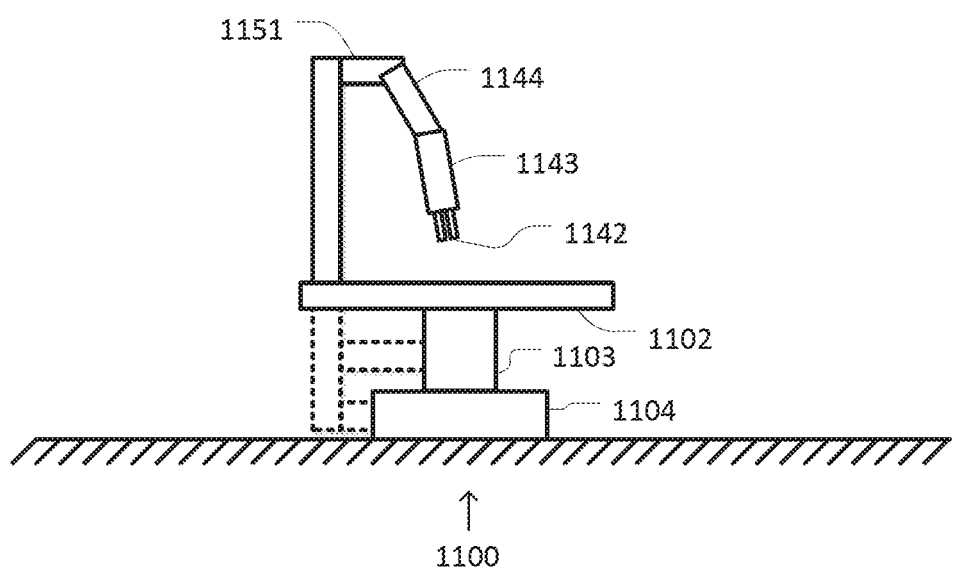

FIG. 7F illustrates another multi-instrument, single-body opening computer-assisted device 1151 mechanically grounded via the surgical table 1100, optionally by being coupled to table top 1102, table support structure 1103, or table base 1104. The descriptions above with reference to FIG. 7D also applies to the mechanical grounding options illustrated in FIG. 7F. Computer-assisted device 1151 and surgical table 1100 work together as described herein.

Figure 7G:
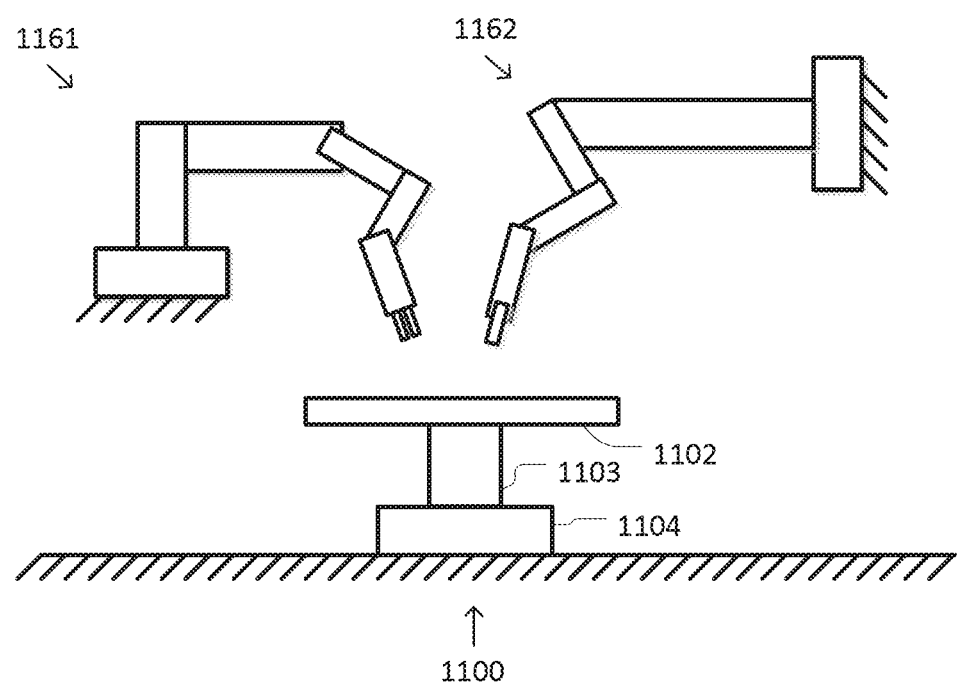

FIG. 7G illustrates that one or more teleoperated multi-instrument, single-body opening computer-assisted devices 1161 and one or more teleoperated single-instrument computer-assisted devices 1162 may be combined to operate with surgical table 1100 as described herein. Each of the computer-assisted devices 1161 and 1162 may be mechanically grounded, directly or via another structure, in various ways as described above.

Figure 3:
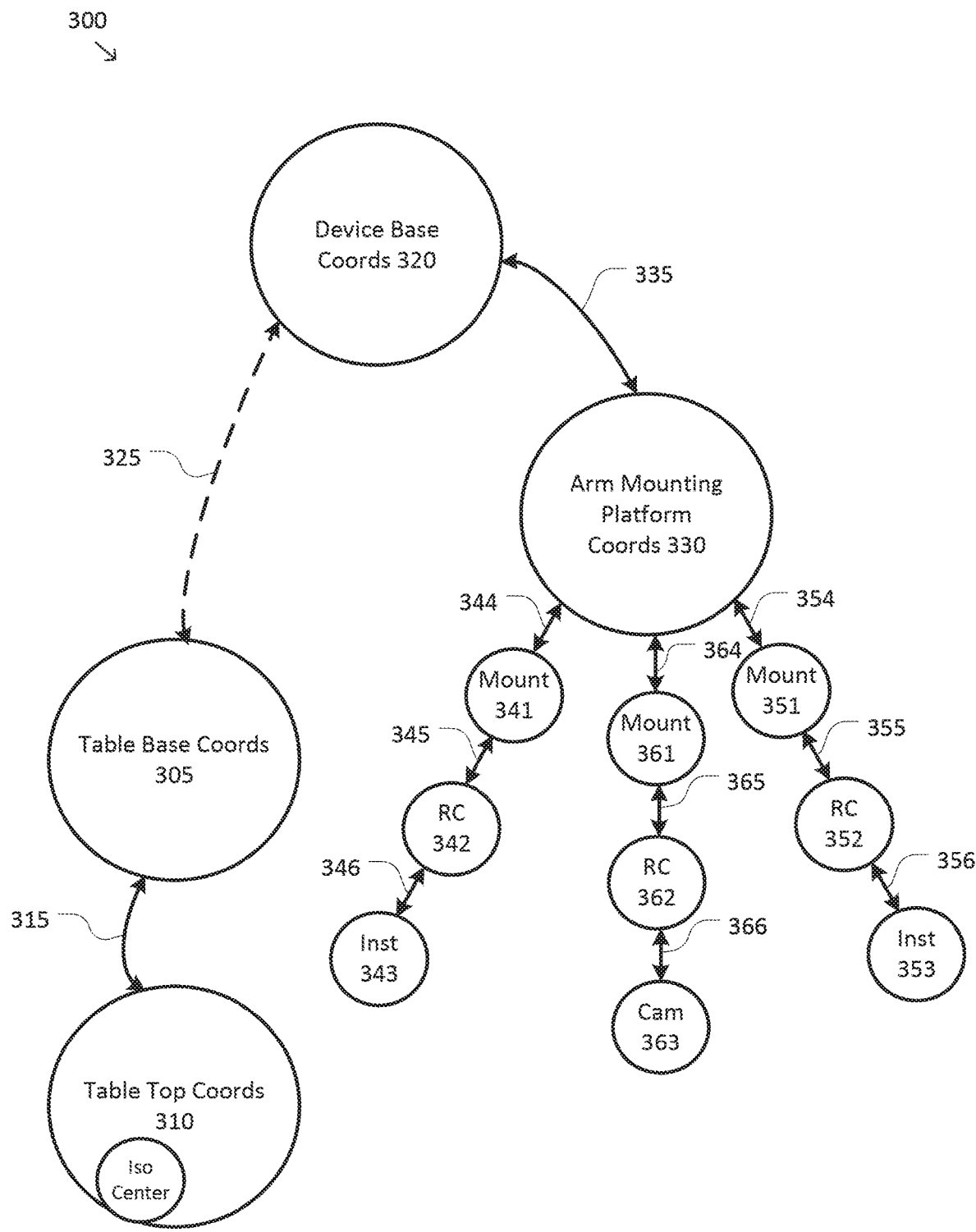
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. The kinematic information may be based on known kinematic models for the links and joints of a computer-assisted medical device and a surgical table. The kinematic information may be further based on information associated with the position and/or orientation of the joints of the computer-assisted medical device and the surgical table. In some examples, the information associated with the position and/or orientation of the joints may be derived from one or more sensors, such as encoders, measuring the linear positions of prismatic joints and the rotational positions of revolute joints.

The kinematic model 300 includes several coordinate frames or coordinate systems and transformations, such as homogeneous transforms, for transforming positions and/or orientation from one of the coordinate frames to another of the coordinate frames. In some examples, the kinematic model 300 may be used to permit the forward and/or reverse mapping of positions and/or orientations in one of the coordinate frames in any other of the coordinate frames by composing the forward and/or reverse/inverse transforms noted by the transform linkages included in FIG. 3. In some examples, when the transforms are modeled as homogenous transforms in matrix form, the composing may be accomplished using matrix multiplication. In some embodiments, a system may use the Denavit-Hartenberg parameters and conventions for attaching coordinate reference frames to one or more points in the kinematic chain and transforming from one reference frame to the other in the kinematic model 300. In some embodiments, the kinematic model 300 may be used to model the kinematic relationships of the computer-assisted device 210 and the surgical table 280 of FIG. 2.

The kinematic model 300 includes a table base coordinate frame 305 that may be used to model a position and/or orientation of a surgical table, such as surgical table 170 and/or surgical table 280. In some examples, the table base coordinate frame 305 may be used to model other points on the surgical table relative to a reference point and/or orientation associated with the surgical table. In some examples, the reference point and/or orientation may be associated with a table base of the surgical table, such as the table base 282. In some examples, the table base coordinate frame 305 may be suitable for use as a world coordinate frame for the computer-assisted system.

The kinematic model 300 further includes a table top coordinate frame 310 that may be used to model positions and/or orientations in a coordinate frame representative of a table top of the surgical table, such as the table top 284. In some examples, the table top coordinate frame 310 may be centered about a rotational center or isocenter of the table top, such as isocenter 286. In some examples, the z-axis of the table top coordinate frame 310 may be oriented vertically with respect to a floor or surface on which the surgical table is placed and/or orthogonal to the surface of the table top. In some examples, the x- and y-axes of the table top coordinate frame 310 may be oriented to capture the longitudinal (head to toe) and lateral (side-to-side) major axes of the table top. In some examples, a table base to table top coordinate transform 315 is used to map positions and/or orientations between the table top coordinate frame 310 and the table base coordinate frame 305. In some examples, one or more kinematic models of an articulated structure of the surgical table, such as articulated structure 290, along with past and/or current joint sensor readings is used to determine the table base to table top coordinate transform 315. In some examples consistent with the embodiments of FIG. 2, the table base to table top coordinate transform 315 models the composite effect of the height, tilt, Trendelenburg, and/or slide settings associated with the surgical table.

The kinematic model 300 further includes a device base coordinate frame that is used to model a position and/or orientation of a computer-assisted device, such as computer-assisted device 110 and/or computer-assisted device 210. In some examples, the device base coordinate frame 320 may be used to model other points on the computer-assisted device relative to a reference point and/or orientation associated with the computer-assisted device. In some examples, the reference point and/or orientation may be associated with a device base of the computer-assisted device, such as the mobile cart 215. In some examples, the device base coordinate frame 320 may be suitable for use as the world coordinate frame for the computer-assisted system.

In order to track positional and/or orientational relationships between the surgical table and the computer-assisted device, it is often desirable to perform a registration between the surgical table and the computer-assisted device. As shown in FIG. 3, the registration may be used to determine a registration transform 325 between the table top coordinate frame 310 and the device base coordinate from 320. In some embodiments, the registration transform 325 may be a partial or full transform between the table top coordinate frame 310 and the device base coordinate frame 320. The registration transform 325 is determined based on the architectural arrangements between the surgical table and the computer-assisted device.

In the examples of FIGS. 7D and 7F, where the computer-assisted device is mounted to the table top 1102, the registration transform 325 is determined from the table base to table top coordinate transform 315 and knowing where the computer-assisted device is mounted to the table top 112.

In the examples of FIGS. 7A-7C, 7E, and 7F, where the computer-assisted device is placed on the floor or mounted to the wall or ceiling, determination of the registration transform 325 is simplified by placing some restrictions on the device base coordinate frame 320 and the table base coordinate frame 305. In some examples, these restrictions include that both the device base coordinate frame 320 and the table base coordinate frame 305 agree on the same vertical up or z-axis. Under the assumption that the surgical table is located on a level floor, the relative orientations of the walls of the room (e.g., perpendicular to the floor) and the ceiling (e.g., parallel to the floor) are known it is possible for a common vertical up or z axis (or a suitable orientation transform) to be maintained for both the device base coordinate frame 320 and the table base coordinate frame 305 or a suitable orientation transform. In some examples, because of the common z-axis, the registration transform 325 may optionally model just the rotational relationship of the device base to the table base about the z-axis of the table base coordinate frame 305 (e.g., a $\theta_Z$ registration). In some examples, the registration transform 325 may optionally also model a horizontal offset between the table base coordinate frame 305 and the device base coordinate frame 320 (e.g., a XY registration). This is possible because the vertical (z) relationship between the computer-assisted device and the surgical table are known. Thus, changes in a height of the table top in the table base to table top transform 315 are analogous to vertical adjustments in the device base coordinate frame 320 because the vertical axes in the table base coordinate frame 305 and the device base coordinate frame 320 are the same or nearly the same so that changes in height between the table base coordinate frame 305 and the device base coordinate frame 320 are within a reasonable tolerance of each other. In some examples, the tilt and Trendelenburg adjustments in the table base to table top transform 315 may be mapped to the device base coordinate frame 320 by knowing the height of the table top (or its isocenter) and the $\theta_Z$ and/or XY registration. In some examples, the registration transform 325 and the table base to table top transform 315 may be used to model the computer-assisted surgical device as if it were attached to the table top even when this is architecturally not the case.

The kinematic model 300 further includes an arm mounting platform coordinate frame 330 that is used as a suitable model for a shared coordinate frame associated with the most proximal points on the articulated arms of the computer-assisted device. In some embodiments, the arm mounting platform coordinate frame 330 may be associated with and oriented relative to a convenient point on an arm mounting platform, such as the arm mounting platform 227. In some examples, the center point of the arm mounting platform coordinate frame 330 may be located on the arm mounting platform orientation axis 236 with the z-axis of the arm mounting platform coordinate frame 330 being aligned with arm mounting platform orientation axis 236. In some examples, a device base to arm mounting platform coordinate transform 335 may be used to map positions and/or orientations between the device base coordinate frame 320 and the arm mounting platform coordinate frame 330. In some examples, one or more kinematic models of the links and joints of the computer-assisted device between the device base and the arm mounting platform, such as the set-up structure 220, along with past and/or current joint sensor readings may be used to determine the device base to arm mounting platform coordinate transform 335. In some examples consistent with the embodiments of FIG. 2, the device base to arm mounting platform coordinate transform 335 may model the composite effect of the two-part column, shoulder joint, two-part boom, and wrist joint of the setup structure portion of the computer-assisted device.

The kinematic model 300 further includes a series of coordinate frames and transforms associated with each of the articulated arms of the computer-assisted device. As shown in FIG. 3, the kinematic model 300 includes coordinate frames and transforms for three articulated arms, although one of ordinary skill would understand that different computer-assisted devices may include fewer and/or more articulated arms (e.g., one, two, four, five, or more). Consistent with the configuration of the links and joints of the computer-assisted device 210 of FIG. 2, each of the articulated arms may be modeled using a manipulator mount coordinate frame, a remote center of motion coordinate frame, and an instrument or camera coordinate frame, depending on a type of instrument mounted to the distal end of the articulated arm.

In the kinematic model 300, the kinematic relationships of a first one of the articulated arms is captured using a manipulator mount coordinate frame 341, a remote center of motion coordinate frame 342, an instrument coordinate frame 343, an arm mounting platform to manipulator mount transform 344, a manipulator mount to remote center of motion transform 345, and a remote center of motion to instrument transform 346. The manipulator mount coordinate frame 341 represents a suitable model for representing positions and/or orientations associated with a manipulator, such as manipulator 260. The manipulator mount coordinate frame 341 is typically associated with a manipulator mount, such as the manipulator mount 262 of the corresponding articulated arm. The arm mounting platform to manipulator mount transform 344 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 342 is typically associated with a remote center of motion of the instrument mounted on the manipulator, such as the corresponding remote center of motion 274 of the corresponding manipulator 260. The manipulator mount to remote center of motion transform 345 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 345 includes an essentially static translational component that does not change as the manipulator and instrument are operated and a dynamic rotational component that changes as the manipulator and instrument are operated.

The instrument coordinate frame 343 is typically associated with a point on an instrument and/or end effector on an instrument mounted on the articulated arm, such as the corresponding end effector 276 on corresponding instrument 270. The remote center of motion to instrument transform 346 is then based on one or more kinematic models of the links and joints of the computer-assisted device that move and/or orient the corresponding instrument, end effector, and the corresponding remote center of motion, along with past and/or current joint sensor readings. In some examples, the remote center of motion to instrument transform 346 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 346 may further be constrained to reflect that the insertion axis of the shaft of the instrument passes through the remote center of motion and may account for rotations of the shaft and the end effector about the axis defined by the shaft.

In the kinematic model 300, the kinematic relationships of a second one of the articulated arms is captured using a manipulator mount coordinate frame 351, a remote center of motion coordinate frame 352, an instrument coordinate frame 353 (or "instrument reference frame 353"), an arm mounting platform to manipulator mount transform 354, a manipulator mount to remote center of motion transform 355, and a remote center of motion to instrument transform 356. The manipulator mount coordinate frame 351 represents a suitable model for representing positions and/or orientations associated with a manipulator, such as manipulator 260. The manipulator mount coordinate frame 351 is typically associated with a manipulator mount, such as the manipulator mount 262 of the corresponding articulated arm. The arm mounting platform to manipulator mount transform 354 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 352 is associated with a remote center of motion of the manipulator mounted on the articulated arm, such as the corresponding remote center of motion 274 of the corresponding manipulator 260. The manipulator mount to remote center of motion transform 355 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 355 may include an essentially static translational component that does not change as the manipulator and instrument are operated and a dynamic rotational component that changes as the manipulator and instrument are operated.

The instrument coordinate frame 353 is associated with a point on an end effector, instrument, and/or end effector on an instrument mounted on the articulated arm, such as the corresponding end effector 276 on corresponding instrument 270 and/or end effector 276. The remote center of motion to instrument transform 356 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 356 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 356 may be constrained to reflect that the insertion axis of the shaft of the instrument passes through the remote center of motion and accounts for rotations of the shaft and the end effector about the insertion axis defined by the shaft.

In the kinematic model 300, the kinematic relationships of a third one of the articulated arms is captured using a manipulator mount coordinate frame 361, a remote center of motion coordinate frame 362, a camera coordinate frame 363, an arm mounting platform to manipulator mount transform 364, a manipulator mount to remote center of motion transform 365, and a remote center of motion to camera transform 366. The manipulator mount coordinate frame 361 represents a suitable model for representing positions and/or orientations associated with a manipulator, such as manipulator 260. The manipulator mount coordinate frame 361 is typically associated with a manipulator mount, such as the manipulator mount 262 of the corresponding articulated arm. The arm mounting platform to manipulator mount transform 364 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 362 is typically associated with a remote center of motion of the manipulator of the articulated arm, such as the corresponding remote center of motion 274 of the corresponding manipulator 260. The manipulator mount to remote center of motion transform 365 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 365 may include an essentially static translational component that does not change as the manipulator and instrument are operated and a dynamic rotational component that changes as the manipulator and instrument are operated.

The camera coordinate frame 363 is associated with an imaging device, such an endoscope, mounted on the articulated arm. The remote center of motion to camera transform 366 is then based on one or more kinematic models of the links and joints of the computer-assisted device that move and/or orient the imaging device and the corresponding remote center of motion, along with past and/or current joint sensor readings. In some examples, the remote center of motion to camera transform 366 accounts for the orientation at which the shaft, such as the corresponding shaft 272, passes through the remote center of motion and the distance to which the shaft is advanced and/or withdrawn relative to the remote center of motion. In some examples, the remote center of motion to camera transform 366 may be constrained to reflect that the insertion axis of the shaft of the imaging device passes through the remote center of motion and accounts for rotations of the imaging device about the axis defined by the shaft.

In some embodiments, an imaging device associated with camera coordinate frame 363 may stream video to an operator workstation such that a user may view the video stream from camera coordinate frame 363. For example, the video captured by the imaging device may be relayed and displayed on display system 192 of operator workstation 190 of FIG. 1. In some embodiments, the imaging device may be oriented such that it captures video and/or images of an instrument associated with instrument coordinate frame 343 and/or an instrument associated with instrument coordinate frame 353. The instrument associated with instrument coordinate frame 343 and/or the instrument associated with instrument coordinate frame 353 may be operated by the user through a controller, such as input or master controls 195 of FIG. 1. In some embodiments, to allow for intuitive manipulation of the instruments, user commands from the controls may correlate with the coordinate system of the camera coordinate frame 363. For example, commands of up and down, left and right, and in and out using the controllers may translate to movements of the instruments up and down, left and right, and in and out in relation to camera coordinate frame 363. Up and down, left and right, in and out, may be resented by the x, y, and z translational axis of coordinate frame 363. Similarly, roll, pitch, and yaw commands may cause the instrument to roll, pitch, and yaw in relation to the camera coordinate frame. In some embodiments, one or more processors, such as processor 140 of FIG. 1, may translate user commands from the camera coordinate frame 363 to respective commands and motion in the instrument coordinate frames 343 and 353. The translational commands may be through the kinematic relationships. For example, commands to the instrument associated with instrument coordinate frame 343 may go from camera coordinate frame 363 to remote center of motion reference frame 362 using transform 366, then from remote center of motion reference frame 362 to manipulator mount coordinate frame 361 using transform 365, manipulator mount coordinate frame 361 to arm mounting platform coordinate frame 330 using transform 364, arm mounting platform coordinate frame 330 to manipulator mount coordinate frame 341 using transform 344, manipulator mount coordinate frame 341 to remote center of motion coordinate frame 342 using transform 345, and remote center of motion coordinate frame 342 to instrument coordinate frame 343 using transform 346. In this manner, any motion commands known in one reference frame can be transformed to corresponding commands in one or more other coordinate frames.

As discussed above and further emphasized here, FIG. 3 is merely an example which should not unduly limit the scope of the claims. One of ordinary skill in the art would recognize many variations, alternatives, and modifications. According to some embodiments, the registration between the surgical table and the computer-assisted device may be determined between the table top coordinate frame 310 and the device base coordinate frame 320 using an alternative registration transform. When the alternative registration transform is used, registration transform 325 is determined by composing the alternative registration transform with the inverse/reverse of the table base to table top transform 315. According to some embodiments, the coordinate frames and/or transforms used to model the computer-assisted device may be arranged differently dependent on the particular configuration of the links and joints of the computer-assisted device, its articulated arms, its end effectors, its manipulators, and/or its instruments. According to some embodiments, the coordinate frames and transforms of the kinematic model 300 may be used to model coordinate frames and transforms associated with one or more virtual instruments and/or virtual cameras. In some examples, the virtual instruments and/or cameras may be associated with previously stored and/or latched instrument positions, projections of instruments and/or cameras due to a motion, reference points defined by a surgeon and/or other personnel, and/or the like.

As a computer-assisted device, such as computer-assisted devices 110 and/or 210, is being operated, one of the goals is to minimize and/or eliminate the propagation of disturbances and/or movements from one or more joints and/or links of an articulated arm to the position of one or more points of an instrument, link(s), and or joint(s). For example, referring to FIG. 2, a disturbance to one or more of joints 242 and/or links 246 may cause an injury to patient 278 if the disturbance is propagated to end effector 276 (end effector 276 being an exemplary point of interest) while inside of patient 278.

In one mode of operation for the computer-assisted system, one or more joints of the surgical table and joints of the articulated arms may be locked and/or held in place through the use of servo control and/or brakes so that motion of the joints is limited and/or prohibited entirely. In some examples, this allows the joints of the manipulators to control an instrument undisturbed by motion from other joints when accomplishing a desired procedure. In some embodiments, the manipulators may be physically constrained to maintain a remote center of motion and motion of one or more joints that do not make up the manipulator might undesirably cause the remote center of motion to move. In those examples, it may be beneficial to have the joints that do not make up the manipulators be locked in place through physical and/or servo control braking systems. However, there may be instances where allowing movement of the remote center of motion would be desirable, and thus allowing for release of the brakes locking one or more of the joints that may affect the position of the remote center of motion.

In some examples, the instruments may be inserted into a patient during the procedure. In some examples, the position of the instruments may be controlled via teleoperation by a surgeon at an operator console such as workstation 190 of FIG. 1. It may, however, be desirable to support other modes of operation for the computer-assisted system that allow for movement in the articulated arms while the instruments remain inserted into the patient. These other modes of operation may increase the risks relative to modes of operation when the instruments are not inserted into to the patient. In some examples, these risks may include injury to the patient when the instruments are allowed to move relative to the patient, breach of a sterile field, collisions between the articulated arms, and/or the like.

In a general case, these other modes of operation may be characterized by a goal of maintaining a point of an instrument relative to a patient when one or more joints proximal to the instrument are subject to a disturbance that results in a change to positions and/or orientations (i.e., movements) of the one or more joints. Because disturbances in one or more first joints, which may be referred to as disturbed joints, proximal to an instrument results in a change in the position of the instrument, it may be desirable to introduce movement in one or more second or compensating joints that compensate for the movement of the instrument caused by the movement of the disturbed joints. Determining the extent of the disturbance and the amount of compensation depends on the type and nature of the disturbance, such as whether the disturbance is associated with movement of the surgical table or patient, or whether the disturbance is confined to the articulated arm used to control the instrument.

The disturbances associated with these other modes of operation that maintain a position of an instrument may occur when the patient is moving so that the position of the instrument and/or the end effector may be monitored in a local coordinate frame. In some examples, these disturbances may include disturbances caused by allowing motion of the articulated structure in the surgical table (i.e., table movement) or movement of the patient relative to the surgical table. In some examples, it is generally desired to have the articulated arm and the instrument move with the patient so that the position of the instrument relative to the patient does not change. In some examples, this may be accomplished using instrument dragging that may include releasing and/or unlocking one or more joints of the articulated arm and allowing the body wall of the patient at the body opening to drag the remote center of motion and the instrument as the patient moves. In some examples, as the remote center of motion moves the orientation of the instrument relative to the remote center of motion may begin to change resulting in a change between the position of instrument relative to the patient. Examples of systems permitting active continuation of a surgical procedure during surgical table motion are shown in U.S. Provisional Patent Application No. 62/134,207 entitled "System and Method for Integrated Surgical Table," which was filed Mar. 17, 2015, and concurrently filed PCT Patent Application No. PCT/US2015/057656 entitled "System and Method for Integrated Surgical Table" and published as WO2016/069648 A1, both of which are hereby incorporated by reference in their entirety.

Figure 4A:
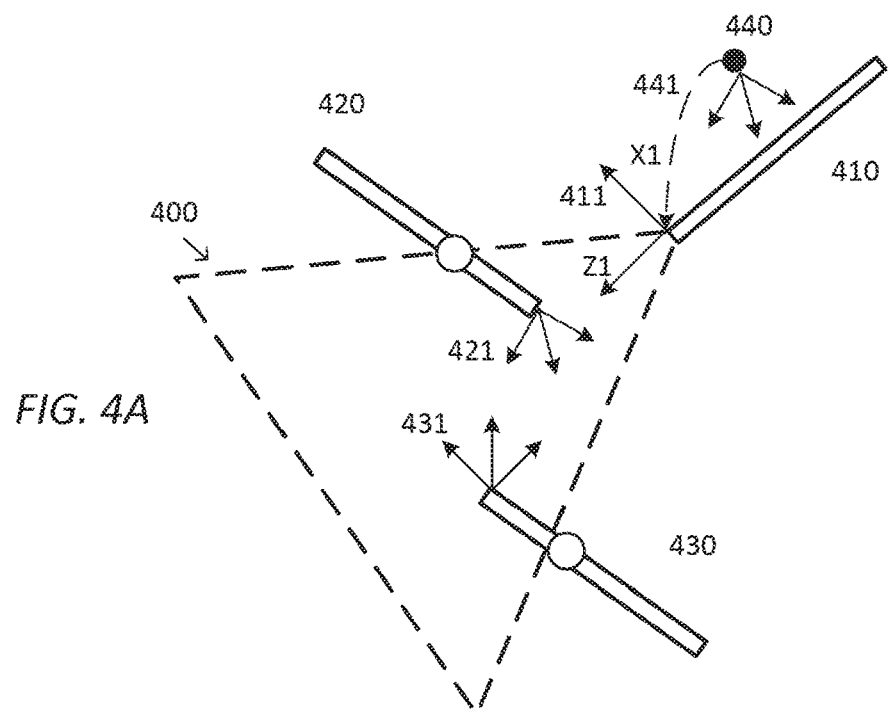
FIG. 4A is a simplified diagram illustrating a perspective view of an exemplary camera view and coordinate systems.
Figure 4B:
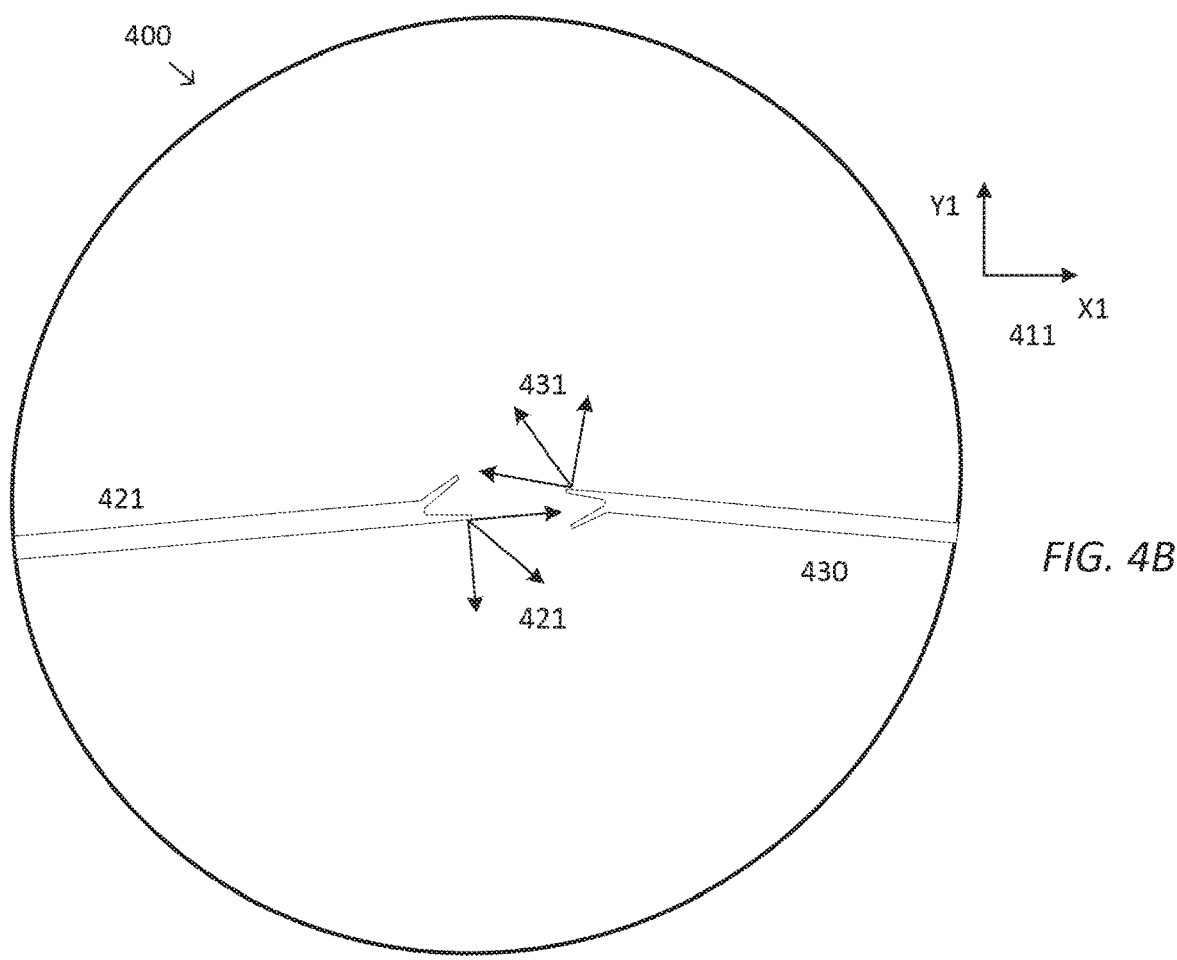
FIG. 4B is a simplified diagram illustrating a camera view from the perspective of a sensor or a display and the related coordinate systems.

FIGS. 4A and 4B illustrate an exemplary camera view 400 from two different perspectives. FIG. 4A may be an overhead perspective, and FIG. 4B may be the perspective of a sensor of imaging device 410. Camera view 400 from the perspective of FIG. 4B may be viewed from a display, such as display system 192 of operator workstation 190 in FIG. 1, receiving streaming image captures from imaging device 410. In some embodiments, imaging device 410 may be an endoscope and may be controlled by an articulated arm, such as articulated arm 102 of FIG. 1 and/or the articulated arm of FIG. 2. In FIG. 4A, camera view 400 is delineated by the dotted line which may represent an exemplary field of view and focus area for imaging device 410. In FIG. 4B, an exemplary camera view 400 is shown from the perspective of a user viewing a video stream from imaging device 410 on a display, such as display system 192 of operator workstation 190 of FIG. 1. In some embodiments, the video stream provided by imaging device 410 may be stereoscopic. Imaging device 410 may use one or more sensors for providing stereoscopic video streams. In this manner, the operator may have a sense of depth perception when using a system such as computer aided system 100 of FIG. 1. Camera coordinate frame 411 illustrates the coordinate frame of imaging device 410. In FIG. 4A, camera coordinate frame 411 shows the Z1 and X1 axes of camera coordinate frame 411 with the Y1 axis (not shown) going in and out of the page. In FIG. 4B the Y1 and X1 axes of camera coordinate frame 411 are shown with the Z1 axis (not shown) going in and out of the page. In some embodiments, camera coordinate frame 411 may be camera coordinate frame 363 of FIG. 3.

FIGS. 4A and 4B also include instruments 420 and 430, which may also be controlled by one or more articulated arms, such as articulated arms 102 of FIG. 1 and/or the articulated arm of FIG. 2. Instruments 420 and 430 may be within camera view 400 and may be manipulated by one or more users or operators using controls, such as input controls 195 of FIG. 1, and viewing instruments 420 and 430 from the perspective of FIG. 4B. FIGS. 4A and 4B also illustrate coordinate frames 421 and 431 of instruments 420 and 430, respectively, from different perspectives. In some examples coordinate frames 421 and 431 may be the same as instrument coordinate frames 343 and 353 of FIG. 3.

Because a user controlling instruments 420 and 430 is viewing the instruments from the perspective of FIG. 4B of camera view 400, it may be useful for user commands to be conducted in the camera coordinate frame 411. Any commands provided in the camera coordinate frame 411 are translated to commands in the coordinate frames 421 and 431 of the instruments, by using a kinematic model, such as kinematic model 300 of FIG. 3. In this manner, up and down may be in relation to the camera view, which may be generally in line of the perspective of the user. A user command to move instrument 420 or 430 up and down may translate to the instrument moving along the Y1 axis of camera coordinate frame 411. Similarly, user commands for other translational motions may follow the X1 and Z1 axes of camera coordinate frame 411. In some embodiments, commands for rotational motions, such as roll, pitch, and yaw, may also be translated from the camera coordinate frame 411 to the coordinate reference frames 421, 431 of the instruments.

In some embodiments, camera coordinate frame 411 may be detached from the physical imaging device 410. For example, camera coordinate frame 440 may be a saved camera coordinate frame for a prior position of imaging device 410 before a movement 441 of imaging device 410. The position of camera coordinate frame 440 may be stored on a computer readable medium, such as memory 150 of FIG. 1. In some embodiments, coordinate frame 440 may be stored as a transformation from a reference coordinate frame, such as arm mounting platform coordinate frame 330, Table top coordinate frame 310, remote center of motion coordinate frame 342, and/or the like of FIG. 3. In some embodiments, camera coordinate frame 440 may be stored as a configuration of an articulated arm based on the position of one or more joints.

Having camera coordinate frame 440 detached from the actual camera may be beneficial when instrument motion is determined in relation to coordinate frame 440. For example, if the position of instruments 420 and 430 were commanded in relation to camera coordinate frame 411 and camera coordinate frame 411 was fixed to imaging device 410, undesirable disturbances to imaging device 410 would translate into undesirable disturbances to instruments 420 and 430. Instead, if the position of instruments 420 and 430 are commanded in relation to a saved coordinate frame, such as camera coordinate frame 440, this problem would not occur because camera coordinate frame 440 is a saved coordinate frame that is potentially independent of any movement of imaging device 410.

In some embodiments, it may be beneficial to latch camera coordinate frame 440 relative to a reference frame, such as table top coordinate frame 310, remote center of motion coordinate frame 342, and/or the like of FIG. 3. Camera coordinate frame 440 may be latched relative to a reference coordinate frame such that when the reference frame moves, camera coordinate frame 440 will also move and maintain distance, orientation, and/or position in relation to the reference coordinate frame. For example, if camera coordinate frame 440 were latched relative to table top coordinate frame 310 of FIG. 3, when the table top physically moved up (moving the table top coordinate frame), coordinate frame 440 would also move up. Similarly, if the table top rotated, camera coordinate frame 440 may also rotate along the same axis as the table. As will be discussed in more detail below, this is beneficial when allowing for table movement. In some embodiments, it may be advantageous to latch camera coordinate frame 440 to the table top coordinate frame during table motion because there may be situation where table motion does not translate to movements in another coordinate frame, such as remote center of motion coordinate frame 342.

In some embodiments, a user may have the option to move and/or realign the camera coordinate frame 440 with the imaging device 410 and camera coordinate frame 411. In this manner when imaging device 410 strays too far from camera coordinate frame 440 such that instrument movements become less intuitive to the user, the user may reset camera coordinate frame 440.

As described previously, as a computer-assisted device, such as computer-assisted devices 110 and/or 210, is being operated it would be desirable to allow continued control of the instrument and/or end effectors while motion of a surgical table, such as surgical tables 170 and/or 280, is allowed. In some examples, this may allow for a less time-consuming procedure as surgical table motion may occur without having to remove instruments that are inserted into the patient. In some examples, this may allow a surgeon and/or other medical personnel to monitor organ movement while the surgical table motion is occurring to obtain a more optimal surgical table pose. In some examples, this may also permit active continuation of a surgical procedure during surgical table motion.

Figure 5:
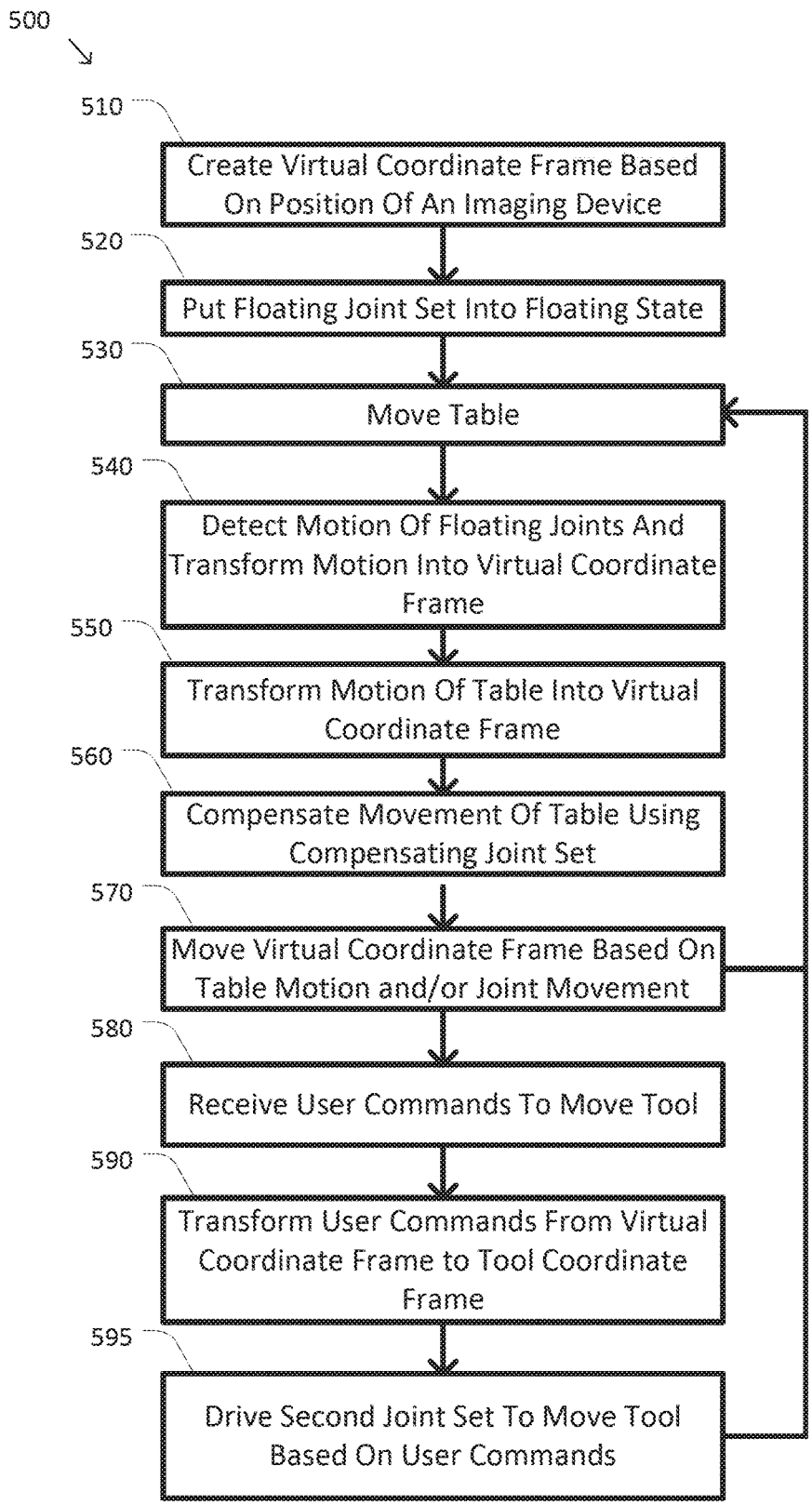
FIG. 5 is a simplified diagram of a method of maintaining control over one or more end effectors while one or more joints of an articulated arm are moved when set to a floating state.

FIG. 5 is a simplified diagram of an exemplary method 500 for maintaining intuitive controls for an end effector on an articulated arm while one or more joints of the articulated arm by being moved by an external force. According to some embodiments, method 500 may include one or more of the processes 510-595 which may be implemented, at least in part, in the form of executable code stored on a non-transitory, tangible, machine readable media that when run on one or more processors (e.g., the processor 140 in control unit 130 of FIG. 1) may cause the one or more processors to perform one or more of the processes 510-595.

At process 510, a coordinate frame and/or configuration for an imaging device may be stored in a memory, such as memory 150 of FIG. 1, creating a virtual coordinate frame. The virtual coordinate frame may be stored in any suitable data structure capable of representing a homogenous transform, such as in the form of one or more matrixes, and/or the like. In some examples, the virtual coordinate frame may be stored in memory in the form of a transform based on a kinematic model for an articulated arm controlling the imaging device. In some embodiments, the virtual coordinate frame may be stored as joint angles, positions and/or configurations on the articulated arm from which the transform may be recomputed using one or more kinematic models of the articulated arm. In some embodiments, the virtual coordinate frame may be stored in memory as a position and orientation in relation to a reference coordinate frame, such as arm mounting platform coordinate frame 330 and/or device base coordinate frame 320 of FIG. 3. In some embodiments, the virtual coordinate frame may be based on a position of an imaging device at a certain point in time, such as before a brake release or before one or more joints for one or more articulated arms is set to a floating state. Joints set to a floating state may generally be referred to as floating joints. In some embodiments, multiple copies of the virtual coordinate frame may be stored, such that each virtual coordinate frame may be modified in relation to multiple situations for a particular articulated arm and/or for different articulated arms. For example, there may be several articulated arms controlling several instruments within view of a single imaging device. Each of the several articulated arms may be positioned in a different manner and there may be one or more virtual camera coordinate frames stored in memory for each articulated arm and in relation to an articulated arm, such as the remote center of motion of the articulated arm. These virtual camera coordinate frames may be modified based on motions to one or more of the articulated arms.

At process 520, one or more joints making up a floating joint set for the articulated arm holding an end effector and/or instrument (herein after "instrument arm") may be put into a floating state. When joints are set in a floating state, the floating joints may move freely upon the introduction of a force. In some embodiments, the articulated arm for an imaging device (hereinafter "imaging arm") may also have a joint set that is put into a floating state. The floating joints, when in a floating state, may be gravity compensated to prevent and/or reduce movements to one or more joints from the force of gravity. In accordance with FIG. 2, set up joints 240 may make up the floating joint set(s) for the instrument arm and/or imaging arm.

In some examples the floating joint set(s) may receive physical motion feedback. In some examples the physical motion feedback may be indirectly caused by a device, such as surgical table 280 of FIG. 2. For example, a remote center of motion of an articulated arm may be placed at a body opening of a patient. The patient may be resting on the surgical table such that when the table moves, the patient is moved. The movement of the patient may cause the body opening of the patient to move, which indirectly causes movement to the articulated arm. This force, in turn, may cause one or more of the floating joints in the joint set(s) to move. This is sometimes referred to as instrument dragging.

However, the floating joints may receive motion feedback from other sources. In some examples, the source of the physical motion feedback may be from an operator pushing and/or pulling on the articulated arm. For example, an operator may pull on the remote center of motion of an articulated arm causing the floating joint set(s) to receive physical motion feedback. In some examples, an operator may be helping to steady one or more articulated arms in connection to a patient while the patient is being moved. One of ordinary skill in the art will recognize that there are several sources of physical motion feedback that may result in changes to the positions and/or orientations of the floating joints, all of which are contemplated herein.

In the following examples for method 500, the physical motion feedback is discussed in relation to a moving surgical table that is communicatively connected and/or registered in some manner with the articulated arm. For example, in FIG. 1, surgical table 170 is communicatively coupled to arms 120 through control unit 130 and device 110. However, one of ordinary skill in the art will recognize that method 500 may be applied to any situation where an object directly and/or indirectly moves the articulated arm independent of whether the object is communicatively connected and/or registered in some manner with the articulated arm. For example, any process in method 500 that uses some communication from the surgical table may be ignored/omitted when method 500 is applied for objects that are not registered. Furthermore, instead of the articulated arms being moved by the surgical table, the articulated arms may be moved by other disturbances.

At process 530, an object, such as a surgical table, may directly and/or indirectly move one of the floating joints of the instrument arm and/or imaging arm. In some embodiments, the surgical table may have several degrees of freedom for movement, such as up/down, left/right, forward/backwards, tilt, Trendelenburg, slide, roll, pitch, yaw, and/or the like. The table movement may be controlled by a controller, such as control unit 130 of FIG. 1. In some embodiments, the controller may be controlling the movement of the table based on user input. In some examples the controller may move the table based on a preprogrammed table movement. In some embodiments, the surgical table may be configured to move a patient that is resting on the table. Though the example above is a surgical table that causes a direct and/or indirect motion to the floating joints, in other embodiments, other devices and/or objects may be causing the direct and/or indirect motion to the articulated arm(s).

At process 540, motion of one or more floating joints of the instrument arm and/or imaging arm caused by the table movement in process 530 is detected. In some embodiments, the instrument arm and/or imaging arm may place the remote center of motion of the instrument arm and/or imaging arm at a patient body opening. The movements in process 530 may move the remote center of motion of the instrument arm and/or imaging arm, which in turn disturbs one of the floating joints of each arm. In some embodiments, the movement of the remote center of motion may be indirect, such as the surgical table moving a patient which in turn causes instrument dragging. A control unit, such as control unit 130, receives indicators that one or more of the floating joints in the instrument arm and/or imaging arm has moved. The indicators may come from sensors in the floating joints providing joint positioning data.

In some embodiments, the detected motion is transformed from a local coordinate frame to the virtual coordinate frame created during process 510. In some embodiments, the transformed motion may be separated into different components such as translational and rotational motions in the virtual coordinate frame.

At process 550, motion readings, data, and/or reports from the surgical table are received and transformed into the virtual coordinate frame. The transformed motion may be separated into the translational and rotational components once transformed into the virtual coordinate frame. For example, in accordance with FIG. 3, table top coordinate frame 310 may change based on the movement of the table. The changes or movement may be transformed from coordinate frame 310 to another coordinate frame, such as remote center of motion coordinate frame 342. Transforming the movement from reference frame of table top coordinate frame 310 to remote center of motion coordinate frame 342, in accordance to FIG. 3, is determined through transforms 325, 344, and 345. The movement of the table are then transformed from the coordinate frame of the remote center of motion to the virtual coordinate frame (not shown) using the transform stored at process 510.

In some embodiments, this process of method 500 may be omitted. For example, process 550 may be omitted when the surgical table, or other object, does not provide and/or report motion readings or provides inaccurate readings.

In some embodiments, process 540 or 550 may be omitted when suitable motion data may be derived from one or the other motion/positioning data. For example, the surgical table may have perfect registration with respect to the instrument arm and/or imaging arm. In some examples, when the surgical table has the same degrees of freedom or motion as the floating arms, the joint positioning data may be sufficient.

At optional process 560, the instrument arm may move a point of interest of the instrument arm, such as the remote center of motion and/or a point on an end effector, using a second set of joints, which may be different from the floating joints, to track and compensate for the motion of the surgical table. These second set of joints may also be referred to as compensating joints of the instrument arm. Compensating joints may generally refer to joints which may be driven or may compensate for other motion. In some cases, the compensating joints may be mutually exclusive from floating joints. Several compensating joints may be referred to as a set of compensating joints and/or as a compensating joint set. This may be beneficial when the floating joints lack one or more degrees of motion in relation to the surgical table. For example, the floating joint set may be unable to rotate and/or translate the remote center of motion, instrument, and/or end effector to maintain orientation with respect to the surgical table and/or patient when the surgical table is moved. When an instrument arm cannot move in relation to a patient being moved, the instrument shaft and/or end effector may move relative to the patient causing injury to the patient and/or the instrument.

In some examples, the second joint set may compensate for the lack of motion in the floating joints by transforming table motion data from the table coordinate frame to the coordinate frame of the point of interest (transformed motion data), isolating the portion of the transformed motion data that the floating joints cannot move, such as rotational motion, and driving the second joint sets to move based on the isolated portion of the translated motion data.

For example, in accordance with FIG. 3, movement in table top coordinate frame 310 is transformed to remote center of motion coordinate frame 342. The transformed movement (in the remote center of motion coordinate frame 342) that the floating joints cannot compensate for is separated from the transformed movement. For example, the transformed movement may be represented as matrix. When the floating joints can translate the remote center of motion but not rotate remote center of motion, the portion of the matrix that represents translational movements is zeroed out and the rotational portions of the matrix left alone. This, in effect, isolates the transformed movement to just the rotational movement. The joints are then driven to move the remote center of motion based on the isolated transformed movement.

Similarly the imaging arm may also move a point of interest of the imaging arm, such as the imaging device and/or a remote center of motion, using a second joint set to track the motion of the surgical table. The method would be the same as with the instrument arm, except motions would be transformed to a coordinate frame related to the imaging device, for example, remote center of motion coordinate frame 352. In this manner, the instruments of the instrument arm maintain their orientation to the table and the imaging device of the imaging arm. As a result, an operator viewing the instruments through images provided by the imaging device would see patient anatomy moving, but the instrument, camera, and patient move in a fixed manner with the table top may appear stationery and/or relatively stationary. This is because the entire camera and instrument may be moving in line or very close to in line with each other and/or the table top.

At process 570 the virtual coordinate frame is moved in relation to the movement of the instrument arm. In some embodiments the virtual coordinate frame is moved in relation to a point of interest on the instrument arm, such as a remote center of motion.

In some examples, the virtual coordinate frame is linked to a point of interest, such as a remote center of motion of the instrument arm. In this manner, as the point of interest of the instrument arm is moved by the table and/or moved to compensate for the table motion. The virtual coordinate frame is moved in relation to the point of interest as if there were a rigid object connecting the virtual coordinate frame with the remote center of motion.

In some examples, the positioning of the virtual coordinate frame is moved to track the point of interest using the joint motion data. For example, the virtual coordinate frame is moved based on the transform of the joint positioning data at process 540 to the coordinate frame of the virtual coordinate frame.

Similarly, the positioning of the virtual coordinate frame is moved to track the point of interest using the surgical table motion data. For example, the virtual coordinate frame is moved based on the transform of the table motion data at process 550 to the coordinate frame of the virtual coordinate frame.

In some embodiments, the virtual coordinate frame may be moved using a combination of the joint motion data and table motion data. For example, the joint motion data of process 540 transformed to the virtual coordinate frame, and table motion of process 550 that is transformed to the virtual coordinate frame and isolated for degrees of motions lacking in the floating arms may be used. In some examples the isolated motions from the table motion may be rotational movement in the virtual coordinate frame.

In some embodiments, the virtual coordinate frame is moved in relation to the movement of another point of interest, such as a table top. The virtual coordinate frame uses the table motion data to change the position of the virtual coordinate frame in relation to the table top. This may be useful when the table can substantially change in orientation without inducing appreciable movement of the remote centers of motion of an articulate arm. For example, isocentered motion.

By moving virtual coordinate frame based on the movement of the table and/or floating joints, the virtual coordinate frame maintains an accurate predicted position of the coordinate frame for the imaging device. Because a user manipulating the instruments may be viewing the instruments through the imaging device and the virtual coordinate frame is a good predictor of the position of the imaging device, a user may not be able to tell the difference between instrument motion commands applied using the virtual coordinate frame and instrument motion commands applied using the actual coordinate frame of the imaging device. This effectively approximates instrument motion commands in the reference frame of the imaging device, even when the imaging device is not perfectly positioned and/or oriented with the virtual coordinate frame.

However, in cases where the virtual coordinate frame has strayed too far from the imaging device, such that a user can tell that the commands are no longer in the coordinate frame of the imaging device, the user may be able to reset the position of the virtual coordinate frame to the actual position of the imaging device.

At process 580, commands to move an instrument and/or end effector of the instrument arm may be received. The instrument motion commands may come from a user manipulating input controls, such as input controls 195. In some examples, the instrument motion commands may be received during table motion.

At process 590, the commands at 580 are transformed from movement commands in the virtual camera coordinate frame to the coordinate frame of the instrument and/or end effector using a kinematic model, such as the kinematic model of FIG. 3. In some examples, compensating joint changes for the instrument arm are determined based on the movement commands in the coordinate frame of the instrument and/or end effector. In some examples, the movement commands in the coordinate frame of the instrument and/or end effector are mapped from the coordinate frame of the end effector to one or more local coordinate systems associated with each of the compensating joints. In effect, this transforms the motion commands from the virtual camera coordinate frame to the instrument and/or end effector coordinate frame and then from the end effector coordinate frame to movements commands relative to the compensating joints of the instrument arm. In some examples, one or more kinematic models are used to transform the movement commands to the each of the coordinate frames. In some examples, the compensating joints may include any of the joints of the articulated arm and/or the manipulator that are not part of the first joint set. Once the movement commands for the respective coordinate frames of each joint are determined, they are used to determine the movements for each of the compensating joints. In some examples, an inverse Jacobian may be used to map the movement commands to movements of the compensating joints. In some examples, the movements in the compensating joints may be applied as joint velocities applied to the compensating joints.

At process 595, the second set of joints is driven to move the instrument and/or end effector in accordance with the transformed commands determined at process 580. In some embodiments, the instruments may be moved and/or driven while the table is in motion. According to some embodiments, one or more of the processes 510-590 may be performed concurrently. For example, user commands driving the joints are superimposed onto the commands to drive the joints based on the table motions such that while the table moves, the floating joints are moved by the table, the compensating joints may move in accordance with process 560 while the compensating joints also are moving in accordance with process 580-590.

As discussed above and further emphasized here, FIG. 5 is merely an example which should not unduly limit the scope of the claims. One of ordinary skill in the art would recognize many variations, alternatives, and modifications. According to some embodiments, one or more of the processes 510-595 may be performed in different orders than the order implied in FIG. 5. In some examples, one or more of the process 510-595 may be performed in any order and/or partially or totally in parallel. In some embodiments, one or more process 510-595 may be omitted/ignored.

Figure 6:
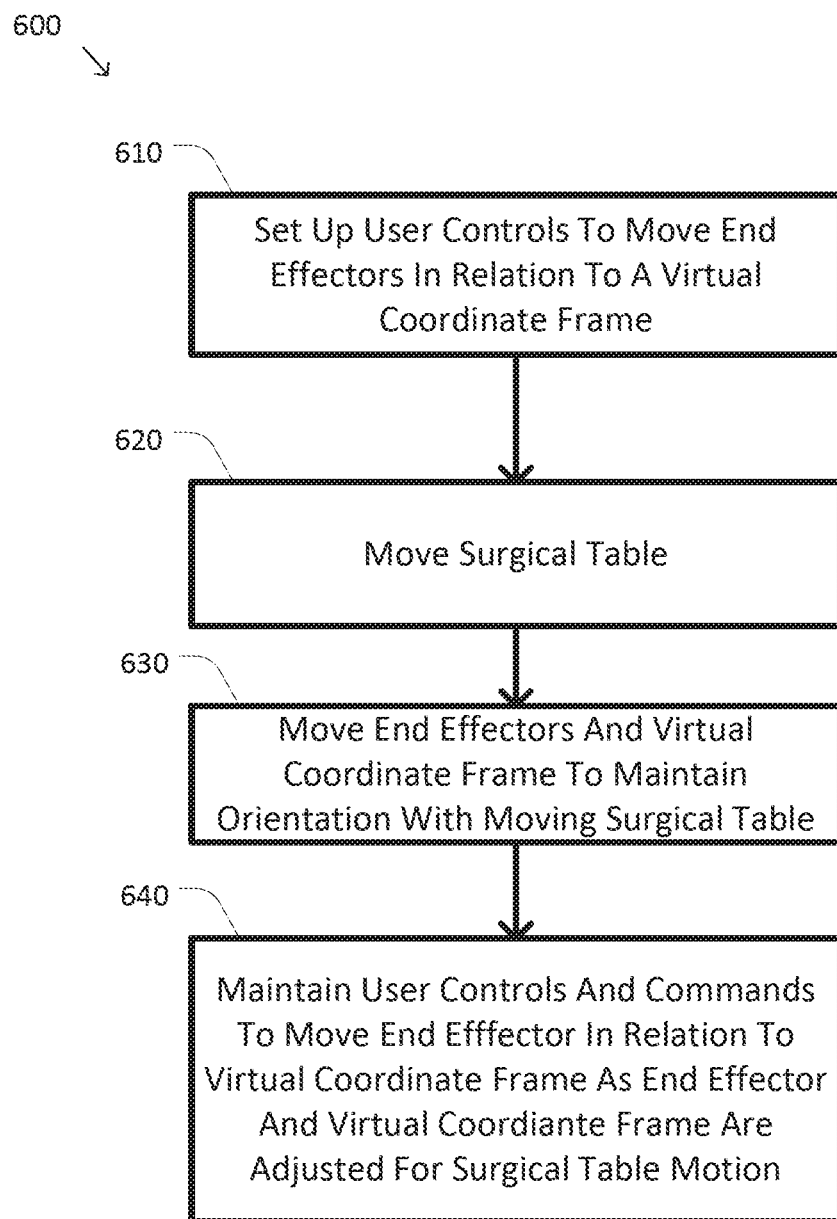
FIG. 6 is a simplified diagram of method for maintaining intuitive controls for an end effector on an articulated arm during table motion.

FIG. 6 is a simplified diagram of method 600 for maintaining intuitive controls for an end effector on an articulated arm during table motion. In some examples a user may be operating one or more end effectors of one or more articulated arms using a controller. In some examples, the end effectors on the one or more articulated arms may be end effectors on articulated arms 120 of FIG. 1. In some example, the user may be controlling the end effectors and the articulated arms through operator workstation 190 of FIG. 1. In some examples, the user may be viewing the one or more end effectors through a display system 192 which may be displaying image captures from an image device on an articulated arm.

At process 610, user controls are set up such that control commands to move an end effector may be conducted in relation to a virtual coordinate frame of an imaging device. In some embodiments the virtual coordinate frame is created using process 510 of FIG. 5. In some examples, received user commands are transformed from movement commands in the virtual camera coordinate frame to the coordinate frame of the instrument and/or end effector using a kinematic model, such as the kinematic model of FIG. 3.

At process 620, a surgical table is moved, which may directly and/or indirectly physically move a patient resting on the table, the articulated arms, the end effectors, and/or the imaging device. The surgical table movement may be in response to user commands to translate and/or rotate the table. In some embodiments, the articulated arms may have a set of joints that are in a floating state such that the table may directly and/or indirectly move the floating joints.

At process 630, the end effectors, imaging device and/or the virtual coordinate frame are moved to maintain relative distance and orientation with the table top of the surgical table as the table moves. For example, if the table top moves up, at process 630 the end effectors, imaging device and the virtual coordinate frame also moves up. Also, if the table top rotates, the imaging device, end effectors, and virtual coordinate frame are rotated along the same axis as the axis of the table top. In this manner, to a user viewing images captured by the imaging device, the user would perceive anything not maintaining orientation with the table top during table motion (e.g. unsecured patient anatomy) as moving. In contrast, the user would perceive the table top and objects either constrained to the table top or maintaining orientation with the table top as stationary.

In some examples, the movements to the end effector and imaging device may be approximations through instrument dragging. In some examples the movements to the end effector and imaging device may be compensation movements of one or more joint to maintain relative position of an end effector in relation to the table top during table motion. In some examples, movement of the virtual coordinate frame is based on table and/or table top motion data during table motion. For example, the virtual coordinate frame may be latched in relation to the table top, and as the table top is moved, the virtual coordinate frame is also moved to maintain orientation and position with the table top. Process 630 may implement one or more processes of FIG. 5 such as processes 540-570.

At process 640, user controls and commands are continually configured to move the end effector in relation to the virtual coordinate frame as the virtual coordinate, end effector, and/or imaging device moves according to process 630 with the surgical table as the surgical table is moved according to process 620. In some embodiments, process 640 may be implemented using processes 590-595 of FIG. 5.

As discussed above and further emphasized here, FIG. 6 is merely an example which should not unduly limit the scope of the claims. One of ordinary skill in the art would recognize many variations, alternatives, and modifications. According to some embodiments, one or more of the processes 610-640 may be performed in different orders than the order implied in FIG. 6. In some examples, one or more of the process 610-640 may be performed in any order and/or partially or totally in parallel. In some embodiments, one or more process 610-640 may be omitted/ignored.

Some examples of control units, such as control unit 130 may include non-transient, tangible, machine readable media that include executable code that when run by one or more processors (e.g., processor 140) may cause the one or more processors to perform the processes of method 500. Some common forms of machine readable media that may include the processes of method 500 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted medical device comprising:
   a first articulated arm, the first articulated arm configured to be coupled to an end effector, and the first articulated arm having a first joint set and a second joint set; and
   a control unit that, when coupled to the first articulated arm and a surgical table, is configured to:
      configure one or more joints in the first joint set to a mode where the one or more joints in the first joint set are able to move in response to an external force applied to the first articulated arm;
      detect movement of the first joint set caused by a movement of the surgical table;
      receive an instrument motion command to move the end effector while the surgical table is moving;
      determine first movement of the second joint set to compensate for movement of the end effector caused by the movement of the first joint set due to the movement of the surgical table;
      determine second movement of the second joint set relative to a virtual coordinate frame to perform the instrument motion command, the virtual coordinate frame being of an imaging device capturing images of the end effector, and the virtual coordinate frame being detached from an actual imaging coordinate frame of the imaging device; and
      drive the second joint set based on superimposing the first and second movements.

2. The device of claim 1, wherein the control unit is further configured to transform the instrument motion command from the virtual coordinate frame to a coordinate frame of the end effector.

3. The device of claim 1, wherein the virtual coordinate frame is based on a pose of the imaging device saved prior to the movement of the surgical table.

4. The device of claim 1, wherein the control unit is further configured to maintain the virtual coordinate frame in fixed relationship to a table top of the surgical table.

5. The device of claim 1, wherein the control unit is further configured to drive a third joint set in a second articulated arm based on the movement of the surgical table.

6. The device of claim 1, wherein to determine the first movement, the control unit is further configured to:
   transform the movement of the surgical table in a surgical table coordinate frame into a motion in an end effector coordinate frame.

7. The device of claim 1, wherein to determine the first movement, the control unit is further configured to:
   transform the movement of the surgical table in a surgical table coordinate frame into a motion in a remote center of motion coordinate frame;
   separate a rotational part of the motion in the remote center of motion coordinate frame; and
   determine the first movement based on the rotational part and not a translational part of the motion in the remote center of motion coordinate frame.

8. The device of claim 5, wherein to drive the third joint set based on the movement of the surgical table, the control unit is further configured to:
   transform the movement of the surgical table in a surgical table coordinate frame into a motion in a second virtual coordinate frame; and
   drive the third joint set to move in relation to the motion in the second virtual coordinate frame.

9. The device of claim 5, wherein to drive the third joint set based on the movement of the surgical table, the control unit is further configured to:
   transform the movement of the surgical table in a table coordinate frame into a motion in a second virtual coordinate frame;
   separate a rotational part of the motion in the second virtual coordinate frame; and
   drive the third joint set to move in relation to the rotational part and not a translational part of the motion in the second virtual coordinate frame.

10. A method of controlling motion in a medical device, the method comprising:
   configuring one or more joints in a first joint set of a first articulated arm of the medical device to a mode where the one or more joints in the first joint set are able to move in response to an external force applied to the first articulated arm;
   detecting movement of the first joint set caused by movement of a surgical table;
   receiving an instrument motion command to move an end effector of the first articulated arm while the surgical table is moving;
   determining first movement of a second joint set of the first articulated arm to compensate for movement of the end effector caused by the movement of the first joint set due to the movement of the surgical table;
   determining second movement of the second joint set relative to a virtual coordinate frame to perform the instrument motion command, the virtual coordinate frame being of an imaging device capturing images of the end effector, and the virtual coordinate frame being detached from an actual imaging coordinate frame of the imaging device; and
   driving the second joint set based on a superposition of the first and second movements.

11. The method of claim 10, wherein the virtual coordinate frame is based on a pose of an imaging device saved prior to the movement of the surgical table.

12. The method of claim 10, wherein the method further comprises driving a third joint set in a second articulated arm based on the movement of the surgical table.

13. The method of claim 10, wherein driving the second joint set comprises:
   transforming the movement of the surgical table in a surgical table coordinate frame into a motion in an end effector coordinate frame.

14. The method of claim 10, wherein driving the second joint set comprises:
   transforming the movement of the surgical table in a surgical table coordinate frame into a motion in a remote center of motion coordinate frame;
   separating a rotational part of the motion in the remote center of motion coordinate frame; and
   determining the first movement based on the rotational part and not a translational part of the motion in the remote center of motion coordinate frame.

15. The method of claim 12, wherein driving the third joint set based on the movement of the surgical table comprises:
   transforming the movement of the surgical table in a surgical table coordinate frame into a motion in a second virtual coordinate frame; and
   driving the third joint set to move in relation to the motion in the second virtual coordinate frame.

16. The method of claim 12, wherein driving the third joint set based on the movement of the surgical table comprises:
   transforming the movement of the surgical table in a table coordinate frame into a motion in a second virtual coordinate frame;
   separating a rotational part of the motion in the second virtual coordinate frame; and
   driving the third joint set to move in relation to the rotational part and not a translational part of the motion in the second virtual coordinate frame.

17. A computer-assisted medical device comprising:
   a first articulated arm, the first articulated arm configured to have an end effector; and
   a control unit, when coupled to the first articulated arm and a surgical table, configured to:
      maintain an orientation and position of the end effector in relation to a table top of the surgical table when the surgical table is moved by:
         configuring one or more joints in a first joint set of the first articulated arm of the medical device to a mode where the one or more joints in the first joint set are able to move in response to an external force applied to the first articulated arm;
         detecting movement of the first joint set caused by movement of the surgical table;
         receiving an instrument motion command to move an end effector of the first articulated arm while the surgical table is moving;
         determining first movement of a second joint set of the first articulated arm to compensate for movement of the end effector caused by the movement of the first joint set due to the movement of the surgical table;
         determining second movement of the second joint set relative to a virtual coordinate frame to perform the instrument motion command, the virtual coordinate frame being of an imaging device capturing images of the end effector, and the virtual coordinate frame being detached from an actual imaging coordinate frame of the imaging device; and
         driving the second joint set based on superimposing the first and second movements.

18. The device of claim 17, wherein the control unit is further configured to maintain the orientation and position of the virtual coordinate frame in relation to a table top of the surgical table when the surgical table is moved.

19. The device of claim 18, wherein the control unit is further configured to maintain the orientation and position of an imaging device in relation to a table top of the surgical table when the surgical table is moved.

20. The device of claim 1, wherein the control unit is further configured to realign the virtual coordinate frame with the actual imaging coordinate frame.

21. The device of claim 1, wherein the control unit is further configured to reset a position of the virtual coordinate frame to a position of the imaging device.

22. The method of claim 10, further comprising: realigning the virtual coordinate frame with the actual imaging coordinate frame.

* * * * *